US010136949B2

(12) United States Patent
Felder et al.

(10) Patent No.: US 10,136,949 B2
(45) Date of Patent: Nov. 27, 2018

(54) GATHERING AND ANALYZING DATA FOR ROBOTIC SURGICAL SYSTEMS

(71) Applicant: Ethicon Endo-Surgery, LLC, Guaynabo, PR (US)

(72) Inventors: Kevin D. Felder, Cincinnati, OH (US); Bernard Siu, San Jose, CA (US); Sina Nia Kosari, Menlo Park, CA (US); Pablo Eduardo Garcia Kilroy, Menlo Park, CA (US)

(73) Assignee: Ethicon LLC, Guaynabo, PR (US)

( * ) Notice: Subject to any disclaimer, the term of this patent is extended or adjusted under 35 U.S.C. 154(b) by 359 days.

(21) Appl. No.: 14/827,601

(22) Filed: Aug. 17, 2015

(65) Prior Publication Data
US 2017/0049517 A1 Feb. 23, 2017

(51) Int. Cl.
*A61B 34/10* (2016.01)
*A61B 34/30* (2016.01)
*A61B 34/37* (2016.01)

(52) U.S. Cl.
CPC .............. *A61B 34/10* (2016.02); *A61B 34/30* (2016.02); *A61B 34/37* (2016.02); *A61B 2034/102* (2016.02); *A61B 2034/105* (2016.02); *A61B 2034/107* (2016.02); *A61B 2034/302* (2016.02)

(58) Field of Classification Search
None
See application file for complete search history.

(56) References Cited

U.S. PATENT DOCUMENTS

| 8,831,782 | B2 | 9/2014 | Itkowitz | |
|---|---|---|---|---|
| 2003/0109780 | A1* | 6/2003 | Coste-Maniere | B25J 9/1671 600/407 |
| 2006/0149418 | A1* | 7/2006 | Anvari | A61G 13/10 700/245 |
| 2007/0013336 | A1 | 1/2007 | Nowlin et al. | |
| 2009/0088634 | A1 | 4/2009 | Zhao et al. | |
| 2009/0202387 | A1 | 8/2009 | Dlugos, Jr. et al. | |

(Continued)

FOREIGN PATENT DOCUMENTS

| WO | WO-2014151621 A1 | 9/2014 |
|---|---|---|
| WO | WO-2014151952 A1 | 9/2014 |
| WO | WO-2015095715 A1 | 6/2015 |

OTHER PUBLICATIONS

DiMaio et al., "The da Vinci Research Interface Release 1.01." Insight Journal <http://hdl.handle.net/1926/1464> 1-8 (Jul. 22, 2008).

(Continued)

*Primary Examiner* — Matthew G Marini
(74) *Attorney, Agent, or Firm* — Mintz Levin Cohn Ferris Glovsky and Popeo, P.C.

(57) ABSTRACT

Various exemplary methods, systems, and devices for gathering and analyzing data for robotic surgical systems are provided. In general, the methods, systems, and devices can allow data to be gathered regarding use in a surgical procedure of a robotic surgical system that includes a plurality of movable arms each configured to couple to a surgical instrument. The gathered data can be used to determine a recommended initial position of the arms for future surgical procedures using the robotic surgical system. The recommended initial position can be provided to users of the robotic surgical system in the future surgical procedures.

22 Claims, 12 Drawing Sheets

(56) References Cited

U.S. PATENT DOCUMENTS

| | | |
|---|---|---|
| 2012/0158013 A1 | 6/2012 | Stefanchik et al. |
| 2014/0148816 A1 | 5/2014 | McDonald et al. |
| 2015/0025549 A1* | 1/2015 | Kilroy ................ A61B 19/2203 606/130 |

OTHER PUBLICATIONS

Intuitive Surgical Inc. "Onsite Remote Monitoring." 2014. <http://www.intuitivesurgical.com/support/onsite.html> 2 pages.

Lin et al., "Automatic Detection and Segmentation of Robot-Assisted Surgical Motions." Medical Image Computing and Computer-Assisted Intervention—MICCAI 2005.

International Search Report for Application No. PCT/US2016/046253 dated Dec. 14, 2016 (4 pages).

* cited by examiner

GATHERING AND ANALYZING DATA FOR ROBOTIC SURGICAL SYSTEMS

FIELD

The present disclosure relates generally to gathering and analyzing data for robotic surgical systems.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and one or more trocars are inserted through the incision(s) to form pathway(s) that provide access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is that the systems need to be set up for each surgical procedure to accommodate a variety of factors, such as type of the procedure, surgical approach, patient anatomy, patient physiology, operating room configuration, operating room space, equipment parameters, staffing limitations, and staffing preferences. The setup for each surgical procedure can be time consuming in order for the personnel setting up the system to account for the various factors for the surgical procedure at issue. Surgeons may have preferences for trocar placement and surgical instrument setups for MIS procedures performed without robotic systems, but these instrument setup preferences can be difficult to translate to setting up for use with robotic systems, particularly when the surgeons have no or limited experience with robotic systems. Additionally, incorrect trocar placement and instrument setups can cause any of a variety of problems during performance of the procedure, such as collisions between tools, patient intolerances, inability to access target anatomy, and procedural inefficiencies.

Another drawback with robotic systems is that moving parts of a robotic system can collide with other moving parts of the system and/or with other objects (e.g., tools, tool mounts, personnel, etc.) during the course of a surgical procedure, e.g., as instruments are used on a patient. The collisions can damage the moving parts of robotic system and/or the object(s) with which they collide, can cause patient injury, and/or can prolong the surgical procedure while possible adverse effects or the collision are assessed and/or addressed.

Accordingly, there remains a need for improved methods, systems, and devices for robotic surgical systems.

SUMMARY

The present invention generally provides for gathering and analyzing data for robotic surgical systems. In one embodiment, a system for facilitating performance of surgical procedures is provided that includes a memory configured to store a model profile indicating a suggested setup of a model robotic surgical system for a model surgical procedure, and a processor configured to cause the model profile to be communicated to a user of a robotic surgical system to be used in performance of a surgical procedure on a patient. The robotic surgical system includes a plurality of movable arms each configured to couple to one of a plurality of surgical instruments. The processor is configured to receive movement data indicative of movement of the arms during performance of the surgical procedure on the patient, modify the model profile based on the received movement data, and store the modified model profile in the memory.

The system can vary in any number of ways. For example, the modification of the model profile can be based at least in part on movement of the arms during performance of the surgical procedure from suggested setup positions of the arms provided in the model profile. For another example, the modification of the model profile can be based at least in part on a number of collisions between any of the arms and another object during performance of the surgical procedure. For yet another example, causing the model profile to be communicated to the user can include causing the model profile to be displayed on a display.

For another example, the suggested setup can include at least one of a recommendation of an initial position of each of the arms of the robotic surgical system, a recommendation of an attachment location of each of the arms of the robotic surgical system to a stationary item, a recommendation of an initial position of each of a plurality of trocars relative to the patient on whom the surgical procedure is to be performed using the robotic surgical system, and a recommendation of an initial position of each of the plurality of surgical instruments. The suggested setup can include at least the recommended initial position of each of the arms of the robotic surgical system, and the recommended initial position of each of the arms of the robotic surgical system can include at least one of the arms' position relative to the patient on whom the surgical procedure is to be performed using the robotic surgical system, and the arms' position relative to each other. The suggested setup can include at least the recommended initial position of each of the trocars, and each of the surgical instruments coupled to the arms of the robotic surgical system can be configured to be inserted into the patient through one of the trocars. The suggested setup can include at least the recommended attachment location, and the stationary item can be selected from the group consisting of a table, a wall, a cart, and a ceiling. The suggested setup can include at least the recommended initial position of each of the plurality of surgical instruments, and the recommended initial position of each of the plurality of surgical instruments can include at least one of the instruments' position relative to the patient on whom the surgical procedure is to be performed using the robotic surgical system, and the instruments' position relative to each other.

For another example, the memory can be configured to store a plurality of model profiles each indicating a suggested setup of the model robotic surgical system and each being associated with a different characteristic, the processor can be configured to receive preliminary data indicative of a characteristic associated with the surgical procedure to be performed using the robotic surgical system, and the processor can be configured to, prior to causing the model profile to be communicated, select the model profile from among the plurality of model profiles as the one of the plurality of model profiles associated with the same characteristic as the surgical procedure to be performed on the patient. The characteristic associated with the surgical procedure can include a type of the surgical procedure to be performed using the robotic surgical system, a patient anatomy being targeted in the surgical procedure to be performed using the robotic surgical system, a position of a plurality of trocars being used in the surgical procedure to be performed using the robotic surgical system relative to the patient, a position of a person performing at least a portion of the surgical procedure to be performed using the robotic surgical system, a size of the patient, and an anatomical variation of the patient.

In another embodiment, a system for facilitating performance of surgical procedures includes a processor and a memory. The processor is configured to receive, from each of a plurality of robotic surgical systems, position data indicative of an initial position of each of a plurality of electromechanical arms of the robotic surgical system for use during performance of a surgical procedure using the robotic surgical system. Each of the plurality of arms is configured to be coupled to a surgical instrument. The processor is configured to receive, from each of the plurality of robotic surgical systems, collision data indicative of one or more collisions that occur between two or more of the plurality of arms during performance of the surgical procedure using the robotic surgical system. The processor is configured to analyze the received position data and the received collision data to determine a recommended initial setup of an intended robotic surgical system for use during performance of a surgical procedure on a patient, and cause the recommended initial setup to be provided to a user of the intended robotic surgical system. The memory is configured to store the received position data, the received collision data, and the recommended initial setup.

The system can have any number of variations. For example, the recommended initial setup of the intended robotic surgical system can include at least one of a recommendation of an initial position of each of a plurality of electromechanical arms of the intended robotic surgical system, a recommendation of an attachment location of each of the electromechanical arms of the intended robotic surgical system to a stationary item, a recommendation of an initial position of each of a plurality of trocars relative to the patient on whom the surgical procedure is to be performed using the intended robotic surgical system, and a recommendation of an initial position of each of the plurality of surgical instruments. For another example, the processor can be configured to receive position data indicative of an initial position of each of a plurality of electromechanical arms of the intended robotic surgical system at a start of the surgical procedure to be performed using the intended robotic surgical system, receive collision data indicative of one or more collisions that occur between two or more of the plurality of arms of the intended robotic surgical system during the performance of the surgical procedure using the intended robotic surgical system, analyze the received position data for the plurality of robotic surgical systems, the received position data for the intended robotic surgical system, the received collision data for the plurality of robotic surgical systems, and the received collision data for the intended robotic surgical system, modify the recommended initial setup based on the analysis, and cause the modified recommended initial setup to be provided to a second user of a second robotic surgical system for use during performance of a second surgical procedure on a second patient. For yet another example, the processor causing the recommended initial setup to be provided to the user can include causing the recommended initial setup to be displayed on a display. For still another example, the intended robotic surgical system can include the processor, or a computer system remotely located from the intended robotic surgical system can include the processor.

For another example, the processor can be configured to receive preliminary data indicative of an aspect of the surgical procedure to be performed using the intended robotic surgical system, and the analysis to determine the recommended initial setup can include analysis of the preliminary data, the gathered position data, and the gathered collision data. The aspect of the surgical procedure can include a type of the surgical procedure to be performed using the intended robotic surgical system, a patient anatomy being targeted in the surgical procedure to be performed using the intended robotic surgical system, a position of a plurality of trocars being used in the surgical procedure to be performed using the intended robotic surgical system relative to the patient, a position of a person performing at least a portion of the surgical procedure to be performed using the intended robotic surgical system, a size of the patient, and an anatomical variation of the patient.

In another aspect, a method for facilitating performance of surgical procedures is provided that in one embodiment includes, for each of a plurality of robotic surgical systems, gathering position data indicative of an initial position of each of a plurality of electromechanical arms of the robotic surgical system for use during performance of a surgical procedure using the robotic surgical system. Each of the plurality of arms are configured to be coupled to a surgical instrument. The method also includes, for each of the plurality of robotic surgical systems, gathering collision data indicative of one or more collisions that occur between two or more of the plurality of arms during performance of the surgical procedure using the robotic surgical system. The method also includes analyzing the gathered position data and the gathered collision data to determine a recommended initial setup of an intended robotic surgical system for use during performance of a surgical procedure on a patient, and providing the recommended initial setup to a user of the intended robotic surgical system.

The method can vary in any number of ways. For example, the recommended initial setup of the intended robotic surgical system can include at least one of a recommendation of an initial position of each of a plurality of electromechanical arms of the intended robotic surgical system, a recommendation of an attachment location of each of the electromechanical arms of the intended robotic surgical system to a stationary item, and a recommendation of an initial position of each of a plurality of trocars relative to the patient on whom the surgical procedure is to be performed using the intended robotic surgical system. The recommended initial setup can include at least the recommended initial position of each of the electromechanical arms of the intended robotic surgical system, and the recommended initial position of each of the electromechanical arms of the intended robotic surgical system includes at least one of the arms' position relative to the patient on whom the surgical procedure is to be performed using the intended robotic surgical system, and the electromechanical arms' position relative to each other. The recommended initial setup can include at least the recommended initial position of each of the trocars, and each of the surgical instruments coupled to the electromechanical arms of the intended robotic surgical system can be configured to be inserted into the patient through one of the trocars. The recommended initial setup can include at least the recommended attachment location, and the stationary item is selected from the group consisting of a table, a wall, a cart, and a ceiling. The suggested setup can include at least the recommended initial position of each of the plurality of surgical instruments, and the recommended initial position of each of the plurality of surgical instruments can include at least one of the instruments' position relative to the patient on whom the surgical procedure is to be performed using the robotic surgical system, and the instruments' position relative to each other. Each of the electromechanical arms of the intended robotic surgical system can be multi-jointed, the recommended initial setup can include at least the recommended initial position of each of the electromechanical arms of the intended robotic surgical system, and the recommended initial position of each of the electromechanical arms of the intended robotic surgical system can include positions of each of the arms' joints.

For another example, the method can include receiving preliminary data indicative of an aspect of the surgical procedure to be performed using the intended robotic surgical system, and the analyzing to determine the recommended initial setup can include analysis of the preliminary data, the gathered position data, and the gathered collision data. The aspect of the surgical procedure can include a type of the surgical procedure to be performed using the intended robotic surgical system, a patient anatomy being targeted in the surgical procedure to be performed using the intended robotic surgical system, a position of a plurality of trocars being used in the surgical procedure to be performed using the intended robotic surgical system relative to the patient, a position of a person performing at least a portion of the surgical procedure to be performed using the intended robotic surgical system, a size of the patient, and an anatomical variation of the patient.

For yet another example, the method can include receiving position data indicative of an initial position of each of a plurality of electromechanical arms of the intended robotic surgical system, receiving collision data indicative of one or more collisions that occur between two or more of the plurality of arms of the intended robotic surgical system during the performance of the surgical procedure using the intended robotic surgical system, analyzing the received position data for the plurality of robotic surgical systems, the received position data for the intended robotic surgical system, the received collision data for the plurality of robotic surgical systems, and the received collision data for the intended robotic surgical system to determine a second recommended initial setup of a second intended robotic surgical system for use during performance of a second surgical procedure on a second patient, modifying the recommended initial setup based on the analysis, and causing the modified recommended initial setup to be provided to a second user of a second robotic surgical system for use during performance of a second surgical procedure on a second patient.

For yet another example, each of the plurality of robotic surgical systems can be remotely located from one another, and the position data and the collision data are gathered over a network.

For still another example, providing the recommended initial setup can include visually indicating the recommended initial setup on a display.

For yet another example, the intended robotic surgical system can be one of the plurality of robotic surgical systems.

For another example, the gathered position data and the gathered collision data can be analyzed by a processor of a computer system. The intended robotic surgical system can include the computer system, or the computer system can be remotely located from the intended robotic surgical system.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF DRAWINGS

This invention will be more fully understood from the following detailed description taken in conjunction with the accompanying drawings, in which.

DETAILED DESCRIPTION

Figure 1:
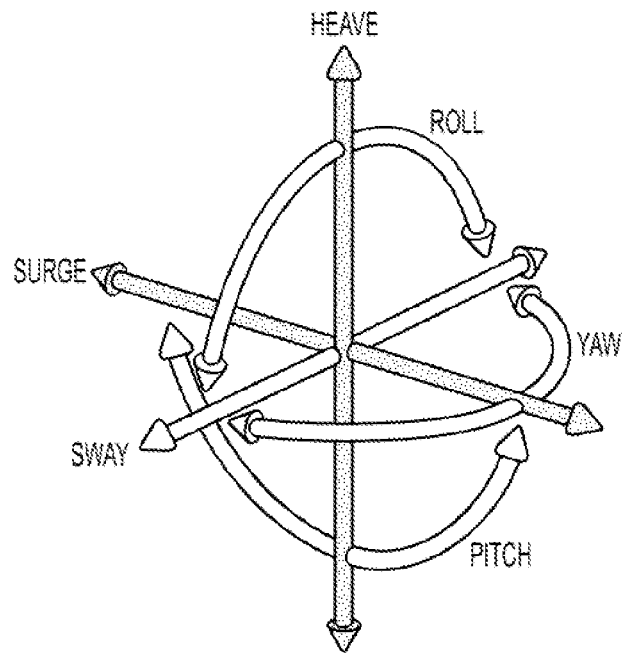
FIG. 1 is a graphical representation of terminology associated with six degrees of freedom.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for gathering and analyzing data for robotic surgical systems are provided. In general, the methods, systems, and devices can allow data to be gathered regarding use in a surgical procedure of a robotic surgical system that includes a plurality of movable arms each configured to couple to a surgical instrument. The gathered data can include data regarding the robotic surgical system's arms, such as information regarding movement of the arms during the course of the surgical procedure and/or information regarding a number of collisions between any of the arms and another object such as another part of the robotic surgical system (e.g., another one of the arms, a base of the robotic surgical system, etc.) or another object in the surgical procedure setting such as a table or a person. The gathered data can be used to determine a recommended initial position of the arms (e.g., a position of the arms at a start of a surgical procedure or a position of the arms at a start of a certain aspect of the surgical procedure for which arm repositioning is preferred or is required) for future surgical procedures using the robotic surgical system. The recommended initial position can be provided to users of the robotic surgical system in the future surgical procedures, which can help reduce chances of arm collisions that occurred and/or other adverse conditions present in the surgical procedure from happening in the future surgical procedures, help facilitate robotic surgical system setup in the future surgical procedures by allowing the recommended initial position to serve as a guide, help a user of the robotic surgical system during the surgical procedure evaluate the effectiveness and/or efficiency of the performed surgical procedure by learning if the recommended initial position of the arms is different from an actual initial position of the arms in the surgical procedure, and/or help share experiences of different users of the robotic surgical system so the users can learn from others' experiences.

In an exemplary embodiment, data from a plurality of robotic surgical systems can be gathered regarding uses of the robotic surgical systems in various surgical procedures. Each of the plurality of robotic surgical systems can include a plurality of movable arms each configured to couple to a surgical instrument. The gathered data regarding the plurality of robotic surgical systems can be used to determine a recommended initial position of arms for future surgical procedures using any of the plurality of robotic surgical systems, and the recommended initial position can be provided to users of the robotic surgical systems to facilitate setting up of the robotic surgical systems for the future surgical procedures. Providing the recommended initial position to users can allow robotic surgical system user experiences to be shared across a surgical community, even when the users of robotic surgical systems are unknown to each other and/or when the users of robotic surgical systems are unlikely to communicate with all other users about their individual uses of any of the robotic surgical systems. Each of the plurality of robotic surgical systems can be remotely located from one another, e.g., located in different hospitals, located in different cities, located in different countries, located in different teaching labs at a university, etc. User experiences in a variety of different locations can thus be analyzed, which can help provide for a more accurate recommended initial setup.

Terminology

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, sway, and by the three rotational or orientation variables, e.g., Euler angles or roll, pitch, yaw, that describe the position and orientation of a component of a surgical system with respect to a given reference Cartesian frame. As used herein, and as illustrated in FIG. 1, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a minimally invasive or invasive surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical system described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical system can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 2:
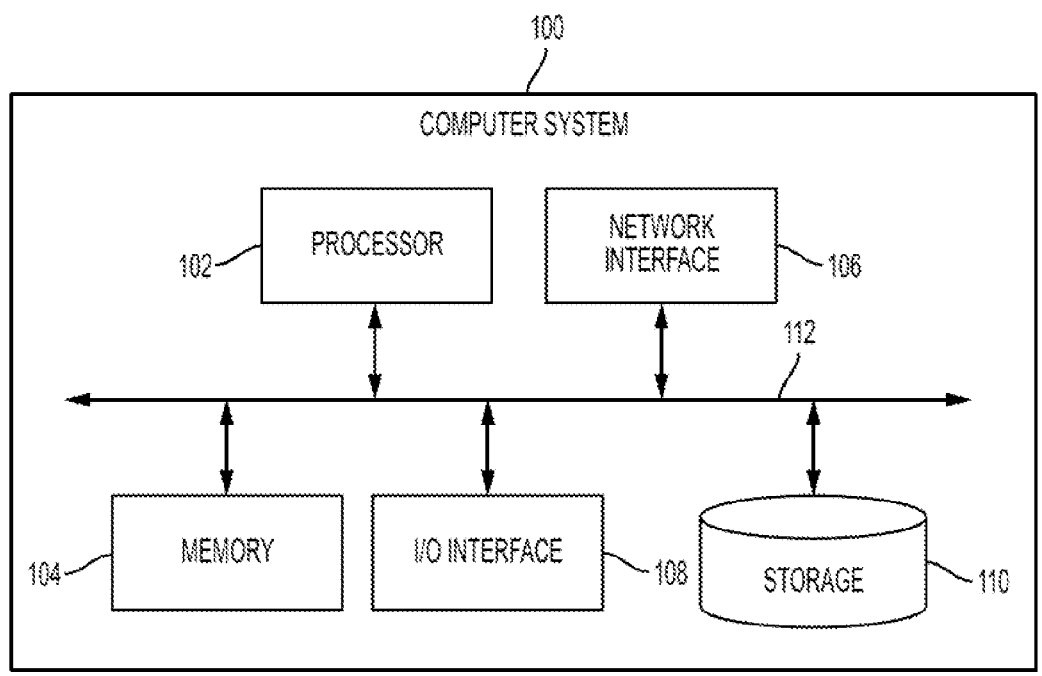
FIG. 2 is a schematic view of one embodiment of a computer system.

FIG. 2 illustrates one exemplary embodiment of a computer system 100. As shown, the computer system 100 can include one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 2 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Robotic Surgical Systems

The systems, devices, and methods disclosed herein can be implemented using a robotic surgical system. Various embodiments of robotic surgical systems are described in further detail in U.S. Pat. No. 8,831,782 filed Jul. 15, 2013 entitled "Patient-Side Surgeon Interface For A Teleoperated Surgical Instrument," Intl. Pat. Pub. No. WO2014151621 filed Mar. 13, 2014 entitled "Hyperdexterous Surgical System," Intl. Pat. Pub. No. WO2014151952 filed Mar. 13, 2014 entitled "Compact Robotic Wrist," and U.S. Pat. Pub. No. 2012/0158013 filed Dec. 17, 2010 entitled "Surgical System And Methods For Mimicked Motion," which are hereby incorporated by reference in their entireties.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 3:
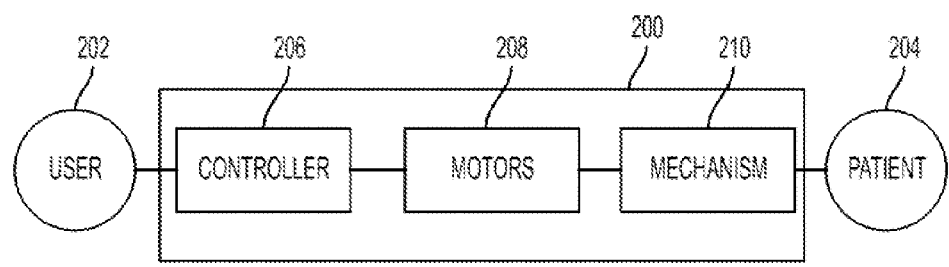
FIG. 3 is a schematic view of one embodiment of a robotic surgical system configured to be operated by a user and to be used during performance of a surgical procedure on a patient.

FIG. 3 illustrates an embodiment of a robotic surgical system 200 configured to be used by a user 202 (e.g., a surgeon, a surgical assistant, etc.) during performance of a surgical procedure on a patient 204. As in this illustrated embodiment, the robotic surgical system 200 can include a controller 206, motors 208, and a movement mechanism 210. The controller 206 can be configured to receive an input from the user 202 requesting movement, relative to the patient 204, of a surgical instrument coupled to the movement mechanism 210. The controller 206 can be configured to cause the motors 208 to drive movement of the movement mechanism 210, thereby causing the movement of the surgical instrument requested by the user 202. Although the illustrated robotic surgical system 200 includes a plurality of motors 208, a robotic surgical system can include a single motor. Similarly, although the illustrated robotic surgical system 200 includes a single controller 206 and a single movement mechanism 210, a robotic surgical system can include a plurality of controllers and/or a plurality of movement mechanisms.

In an exemplary embodiment, the movement mechanism 210 can include an arm. The arm can be configured to move so as to cause movement of a surgical instrument coupled thereto in any one or more of the three translational directions (surge, heave, and sway) and in any one or more of the three rotational directions (roll, pitch, and yaw) in response to control by the controller 206. In an exemplary embodiment, the arm can be configured to provide a plurality of degrees of freedom. More than six degrees of freedom can be provided in a variety of ways, as mentioned above and as will be appreciated by a person skilled in the art. In general, the arm can include a mechanical member configured to move in response to an input to the system 200 from the user 202. The user's input can be configured to cause the controller 206 to transmit an electronic signal to the motors 208 that causes the motors 208 to provide a force (e.g., torque) to the arm, thereby causing movement of the arm. The arm can include a plurality of members jointed together, which can facilitate movement of the arm in a plurality of degrees of freedom via bending, twisting, etc. at various ones of the joints.

The arm can include an electromechanical arm. The electromechanical arm can include one or more mechanical members configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.).

Figure 4:
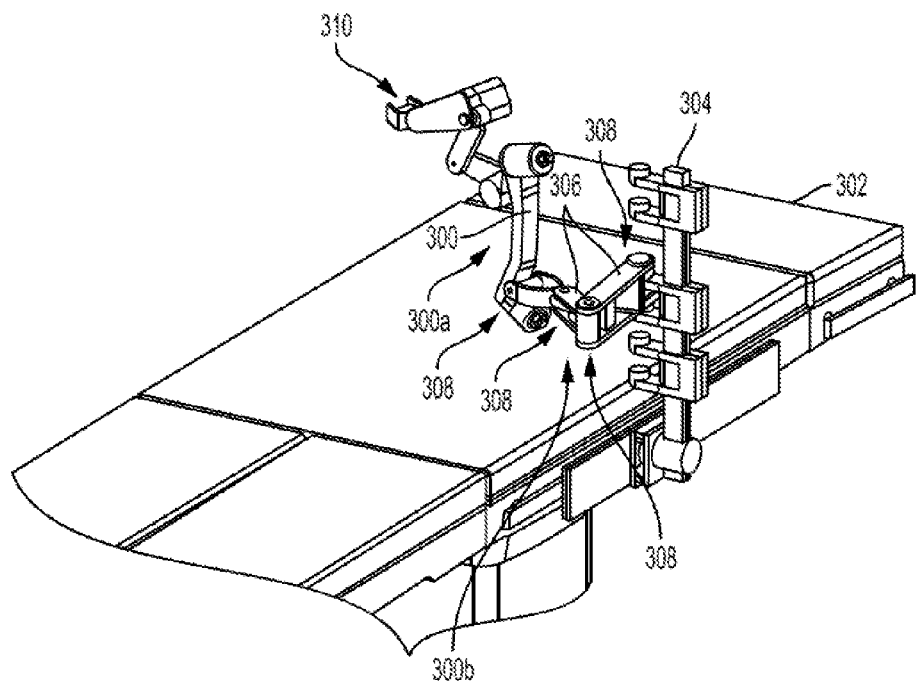
FIG. 4 is a perspective view of one embodiment of an arm of a robotic surgical system, the arm being mounted to a surgical table.
Figure 5:
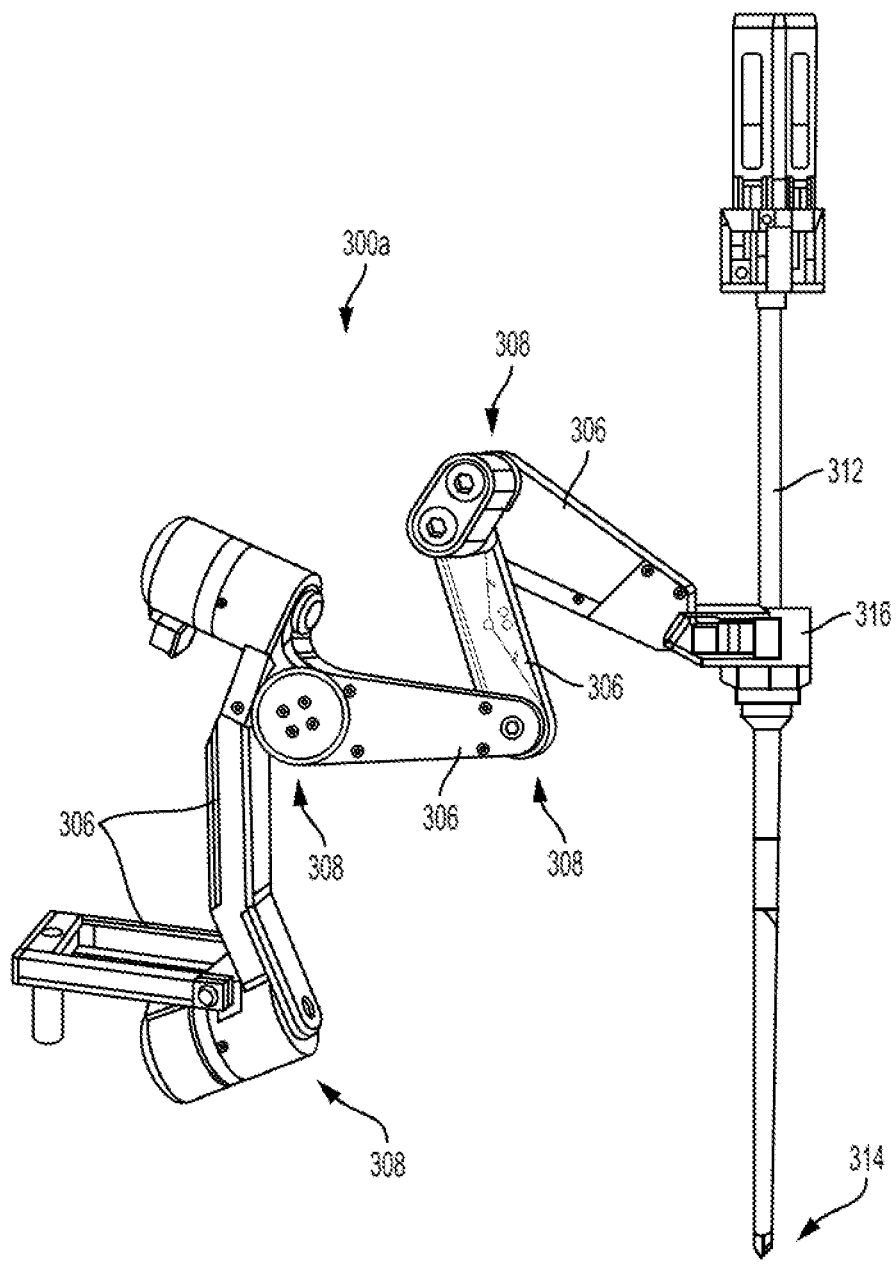
FIG. 5 is a perspective view of an active portion of the arm of FIG. 4.

FIGS. 4 and 5 illustrate an embodiment of an arm 300 in the form of an electromechanical arm. The arm 300 is mounted to a surgical table 302 using a frame 304 in the illustrated embodiment of FIG. 4, but the arm 300 can be mounted to any of a variety of stationary items, a wall, a table, a cart, the ceiling, etc., in any of variety of ways to help stabilize the arm 300 for use during a surgical procedure. The arm 300 can include an active portion 300a configured to be actively controlled, e.g., configured to move in response to electronic input, and a passive portion 300b configured to be passively controlled, e.g., configured to move in response to hand or other manual movement thereof. The passive portion 300b can lack motors or other electrical features, while the active portion 300a can include motors and other electrical features, such as associated with the joints, to facilitate electronic control thereof. In at least some embodiments, an arm can lack a passive portion so as to be configured to be entirely actively controlled. While the active and passive portions 300a, 300b are sometimes referred to herein as components of a single arm, a person skilled in the art will appreciate that the active portion 300a and the passive portion 300b can be separate arms that are matable to each other.

The arm 300 can, as in this illustrated embodiment, include a plurality of mechanical members 306, a plurality of joints 308, and a coupling mechanism 310. Adjacent ones of the mechanical members 306 can be attached together at one of joints 308. In this illustrated embodiment, the active portion 300a of the arm 300 includes five mechanical members 306 and four joints 308, the passive portion 300b of the arm 300 includes two mechanical members 306 and three joints 308, and the arm 300 includes another joint 308 between the active and passive portions 300a, 300b, but arms can have any number of mechanical members and associated joints in its active and passive portions.

As shown in FIG. 5, the arm 300, e.g., the active portion 300a thereof, can be configured to removably and replaceably couple to a surgical instrument 312 via the coupling mechanism 310. A distal end 314 of the instrument 312 can be configured to be advanced into a body of a patient, e.g., through an incision, through a natural orifice, etc. The instrument's distal end 314 can thus include a working end of the instrument 312 configured to facilitate performance of the surgical procedure within the patient. The instrument's distal end 314 can include an end effector, e.g., forceps/graspers, needle drivers, scissors, electrocautery hooks, staplers, clip appliers/removers, suction tools, irrigation tools, etc. As in this illustrated embodiment, the instrument 312 can be advanced into a patient's body through a cannula 316 (e.g., a trocar, an introducer tube, etc.). The coupling mechanism 310 is shown in FIG. 5 coupled to the cannula 316, which has the surgical instrument 312 advanced therethrough.

Aspects of the arm 300 and the frame 304 are further described in previously mentioned Intl. Pat. Pub. No. WO2014151621 filed Mar. 13, 2014 entitled "Hyperdexterous Surgical System" and Intl. Pat. Pub. No. WO2014151952 filed Mar. 13, 2014 entitled "Compact Robotic Wrist."

Figure 6:
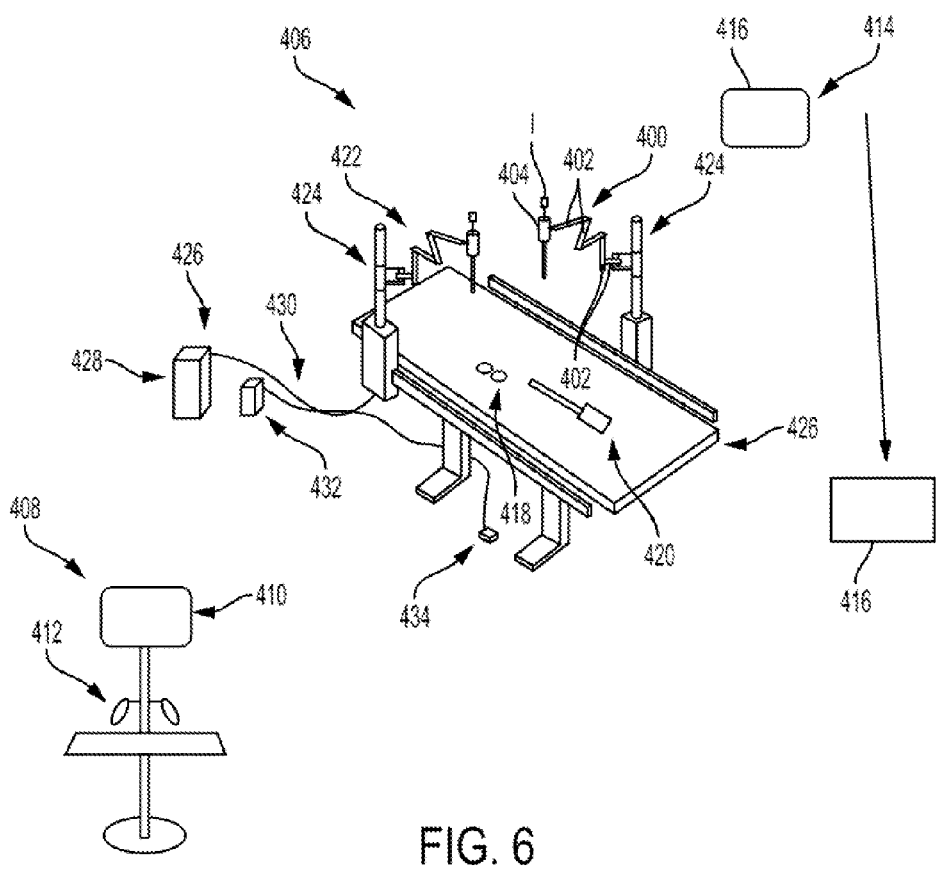
FIG. 6 is a perspective view of one embodiment of a robotic surgical system.

FIG. 6 illustrates another embodiment of an arm 400 in the form of an electromechanical arm. The arm 400 can generally be configured and used similar to the arm 300 of FIGS. 4 and 5. The arm 400 can include a plurality of mechanical members 402, a plurality of joints between adjacent ones of the arms 402, and a coupling mechanism 404 configured to removably and replaceably couple to a surgical instrument I. The arm 400 includes five mechanical members 402 and four joints in this illustrated embodiment, but as mentioned above, arms can have any number of mechanical members and associated joints.

Figure 7:
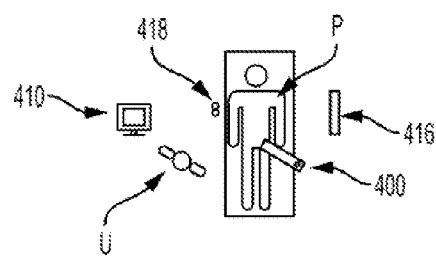
FIG. 7 is a schematic view of one embodiment of the robotic surgical system of FIG. 6 in use during performance of a surgical procedure on a patient.
Figure 8:
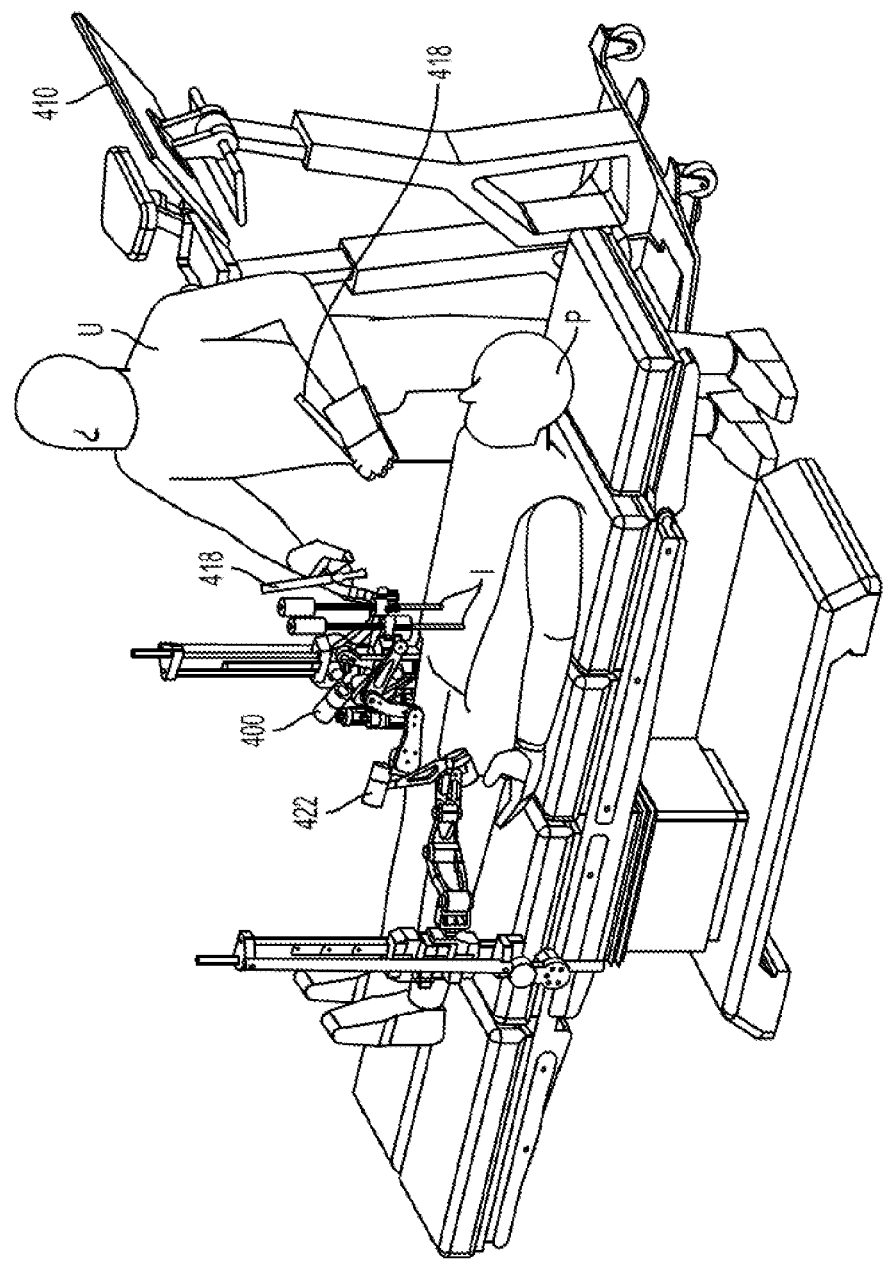
FIG. 8 is a perspective view of the robotic surgical system of FIG. 7 in use during performance of the surgical procedure on a patient.

As shown in FIGS. 6 and 7, the arm 400 can be included in a robotic surgical system 406 configured to facilitate performance of a surgical procedure on a patient P. FIG. 8 shows an example of the system 406 in use. As in this illustrated embodiment, the system 406 can include a user interface sub-system 408 that can include at least one display 410 configured to display information thereon to a user U, at least one user input device 412 configured to receive a user input thereto to control movement of the arm 400, a visualization system 414 that can include at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arm 422 that can be configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 can, as in this illustrated embodiment, include at least one computer 428, one or more cables 430, and at least one power supply 432. The computer 428 can include at least one processor (not shown). As mentioned above, some embodiments of control systems can be at least partially wireless, in which case at least some of the cables 430 need not be present. The robotic surgical system 406 can include at least one foot pedal 434 coupled to the computer 428 via one of the cables 430, which can allow the foot pedal 434 to serve as a user input device. The robotic surgical system 406 can include at least one knee control (not shown) coupled to the computer 428 via one of the cables 430, similar to a knee control of a sewing machine, which can allow the knee control to serve as a user input device.

The robotic surgical system 406 can include a frame 424 for each of the arms 400, 422. The frames 424 in this illustrated embodiment are each mounted to a surgical table 426, but as mentioned above, frames can be mounted elsewhere. The frame 424 in this illustrated embodiment includes a vertical extension movably coupled to a rail mounted to the table 426. The vertical extension can be configured to move along the rail, thereby facilitating positioning of the arms 400, 422 relative to the patient P.

One or more manually operated surgical instruments 420, e.g., instruments not under the control of the robotic surgical system 406, can be used to perform the surgical procedure being performed on the patient P.

Aspects of the robotic surgical system 406 are further described in previously mentioned Intl. Pat. Pub. No. WO2014151621 filed Mar. 13, 2014 entitled "Hyperdexterous Surgical System."

Figure 9:
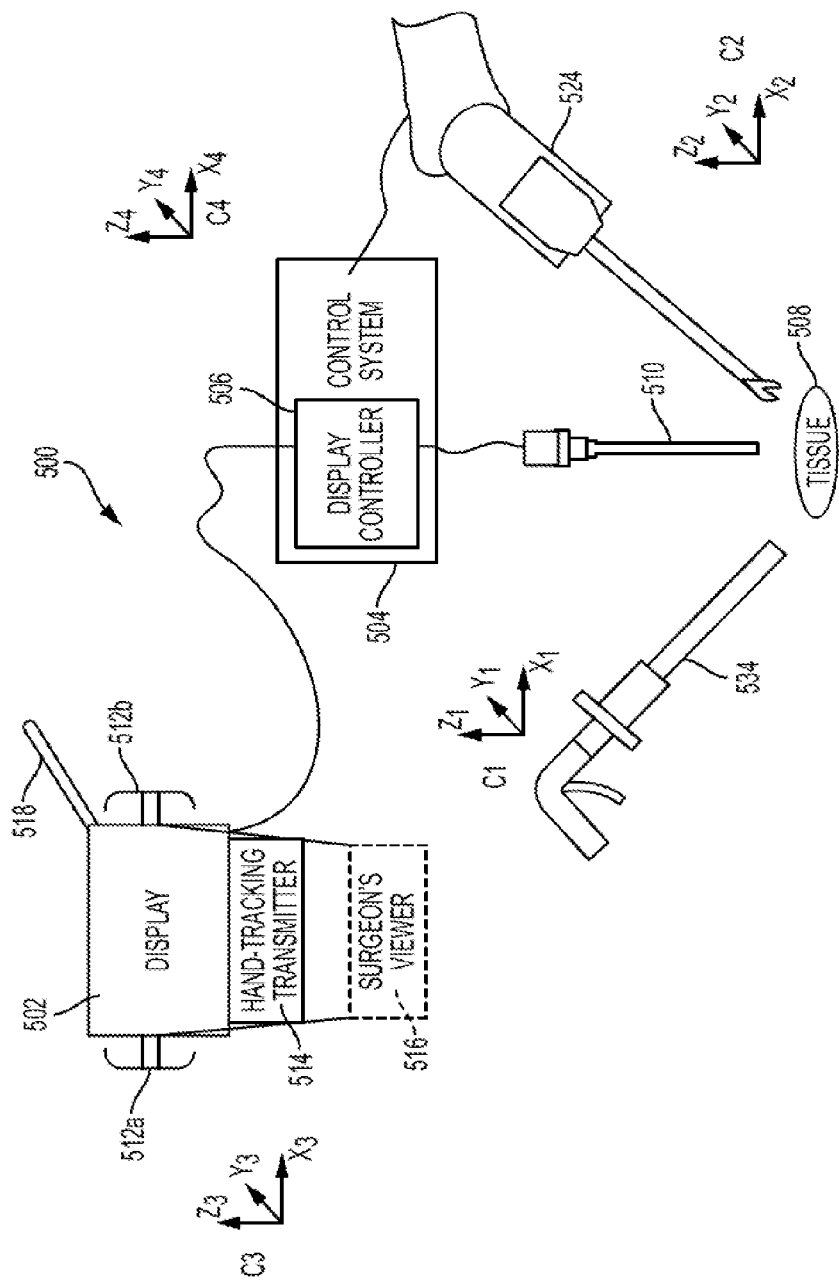
FIG. 9 is a schematic and perspective view of another embodiment of a robotic surgical system.

FIG. 9 illustrates another embodiment of a robotic surgical system 500. As in this illustrated embodiment, the robotic surgical system 500 can include a display 502 and a control system 504 configured to be in electronic communication with the display 502. The display 502 and the control system 504 are in wired electronic communication in this illustrated embodiment, but the electronic communication can be wireless. The control system 504 can include a computer system including a display controller 506 configured to facilitate the display of images on the display 502, such as images of tissue 508 visualized by an endoscope 510 coupled to the control system 504. The display 502 can be coupled to handles 512a, 512b configured to facilitate manual movement of the display 502, a hand-tracking transmitter 514 configured to generate a field (e.g., an electromagnetic field, an optical field (e.g., light beams), etc.), a surgeon's viewer 516 (e.g., glasses, etc.) configured to facilitate three-dimensional (3-D) viewing of 3-D images shown on the display 502, and a boom 518 configured to mount the display 502 to a stable surface (e.g., a wall, a table, etc.). The display 502 can be configured to show two-dimensional (2-D) and/or 3-D images.

Figure 10:
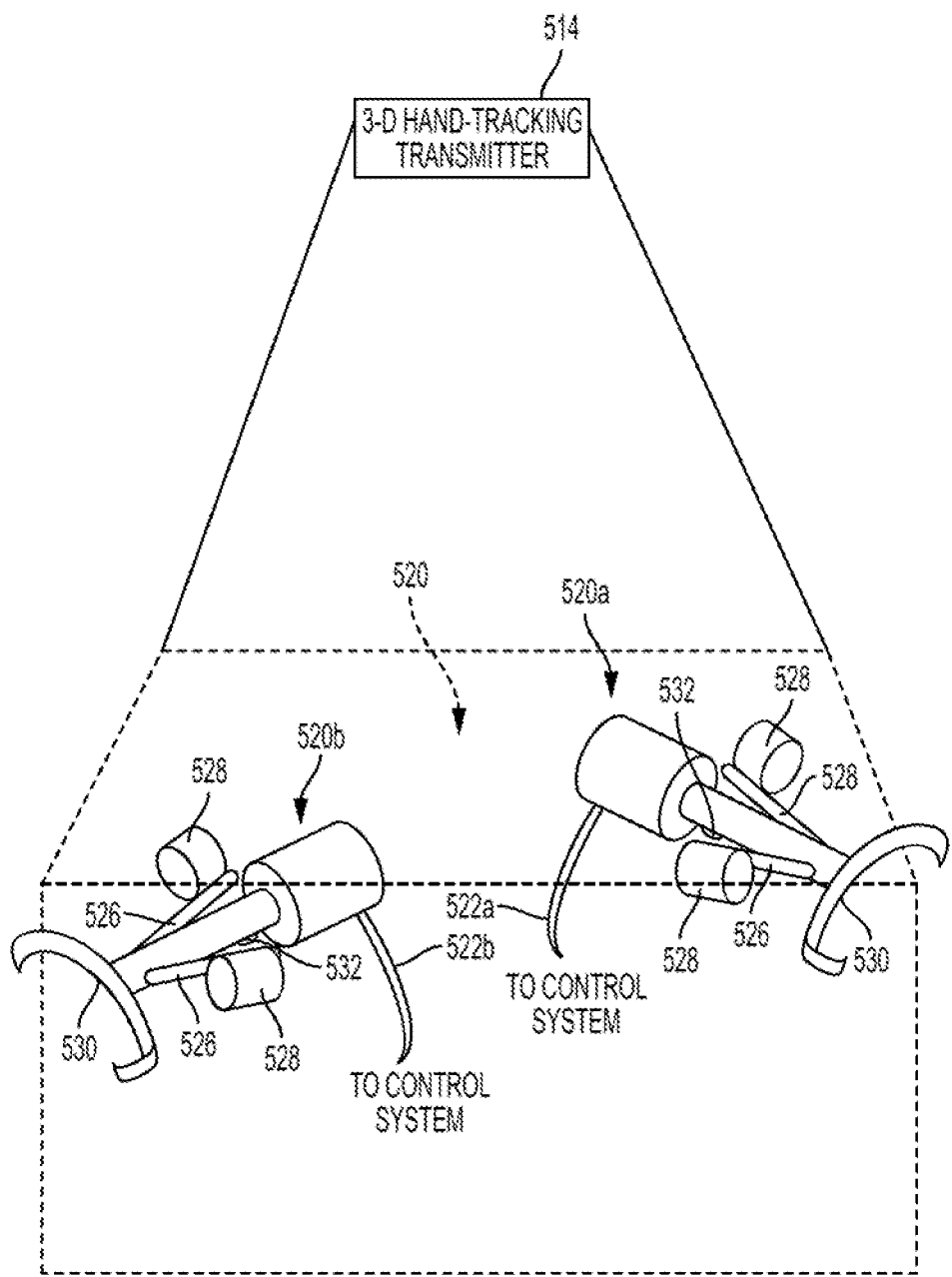
FIG. 10 is a perspective view of one embodiment of a master tool in a field generated by a transmitter of the robotic surgical system of FIG. 9.

Movement of a user-controlled master tool 520, an embodiment of which is illustrated in FIG. 10, in the field generated by the transmitter 514 can be configured to provide sensed spatial position and orientation information in a 3-D coordinate system. The master tool 520 can be configured to transmit the spatial position and orientation information to the control system 504, such as by cables 522a, 522b. The control system 504, e.g., a processor of the control system 504, can be configured to receive the transmitted spatial position and orientation information and, in response thereto, cause a slave tool 524 to move in accordance with the user's movement of the master tool 520. The robotic surgical system 500 can thus allow control of the slave tool 524 via the master tool 520. The master tool 520 in this illustrated embodiment includes first and second master tool grips 520a, 520b that each include a plurality of levers 526, a plurality of finger loops 528, a palm rest 530, and a mode control button 532, but the master tool 520 can have a variety of other configurations, as will be appreciated by a person skilled in the art. The robotic surgical system 500 can include any number of master tools and any number of slave tools each configured to be controlled by the master tool(s).

One or more manually operated surgical instruments 534 can be used to manipulate the tissue 508 in addition to the slave tool 524 that can manipulate the tissue 508.

FIG. 9 illustrates first, second, third, and fourth coordinate systems C1, C2, C3, C4 representing local coordinates that specify the respective position and orientation of the portion of the system 500 with which they are associated. The first coordinate system C1 is associated with the manually operated surgical instrument 534. The second coordinate system C2 is associated with the slave tool 524. The third coordinate system C3 is associated with a user (not shown) visualizing the display 502, and hence also with the master tool 520 configured to be manipulated by the user. The fourth coordinate system C4 is associated with the control system 506, and hence also with images that the control system 506 causes to be displayed on the display 502. In general, the control system 506 can be configured to map and translate the third coordinate system C3 into the second coordinate system C2, e.g., map and translate movement of the master tool 520 to movement of the slave tool 524. The control system 506 can be configured to always orient the display 502 so that the first, second, and third coordinate systems C1, C2, C3 are aligned to the third coordinate system C3. For example, if the user is holding the master tool 520, e.g., one of the first and second master tool grips 520a, 520b, in one of his/her hands and moves that hand to his/her right, thereby moving the held master tool 520 to the right, the control system 506 can be configured to correspondingly cause a working end of the slave tool 524 to move to the right. This movement can be accomplished by the control system 506 causing an arm to which the slave tool 524 is coupled, similar to the arms discussed herein, to move. This movement of the slave tool 523 can "correct" for pivoting of a trocar (not shown) through which the slave tool 524 may be inserted to access the tissue 508.

Aspects of the robotic surgical system 500 are further described in previously mentioned U.S. Pat. No. 8,831,782 filed Jul. 15, 2013 entitled "Patient-Side Surgeon Interface For A Teleoperated Surgical Instrument."

Figure 11:
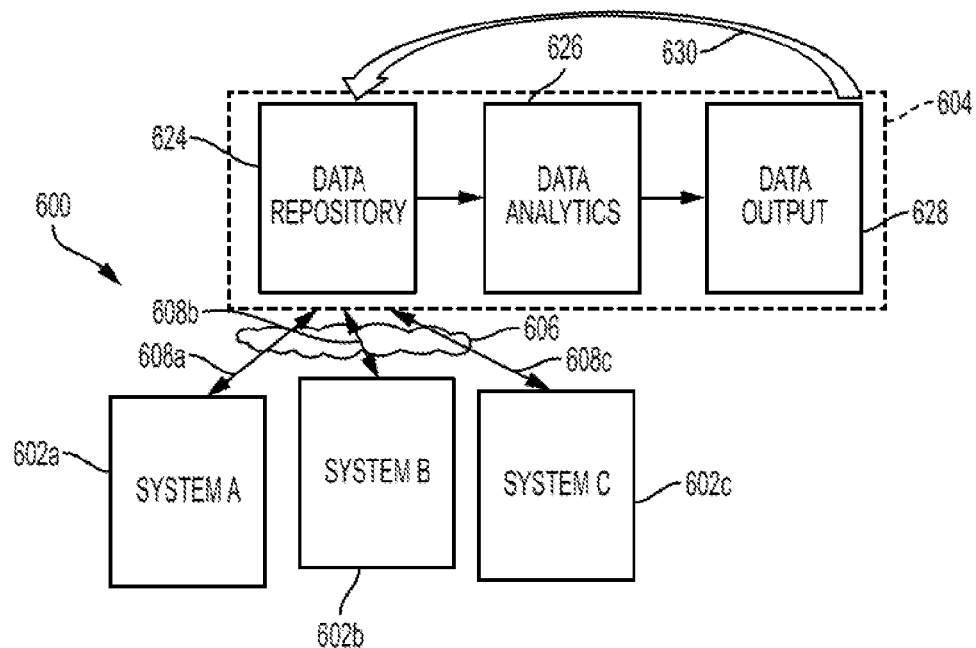
FIG. 11 is a schematic view of one embodiment of a networked system including a control system and a plurality of robotic surgical systems.

As mentioned above, data can be gathered regarding use of a robotic surgical system in a surgical procedure, and the data can be analyzed to determine a recommended robotic surgical system setup for a future surgical procedure. FIG. 11 illustrates an embodiment of a networked system 600 configured to facilitate the collection of data from one or more robotic surgical systems 602a, 602b, 602c and to facilitate determination of a recommended robotic surgical system setup based at least in part on the collected data. In this illustrated embodiment, the networked system 600 includes a control system 604 configured to communicate with each of the robotic surgical systems 602a, 602b, 602c over a network 606 (e.g., the Internet, a LAN, etc.) using one or more communication lines 608a, 608b, 608c. All the communication lines 608a, 608b, 608c can be wired, all the communication lines 608a, 608b, 608c can be wireless, or at least one of the communication lines 608a, 608b, 608c can be wired and a remainder of the communication lines 608a, 608b, 608c can be wireless. Electronic communication via each of the communication lines 608a, 608b, 608c can be implemented in any of a variety of ways, such as by using Transmission Control Protocol/Internet Protocol (TCP/IP), an Open Systems Interconnection (OSI) model, Internetwork Packet Exchange/Sequenced Packet Exchange (IPX/SPX), X.25, AX.25, AppleTalk, etc., as will be appreciated by a person skilled in the art. The robotic surgical systems 602a, 602b, 602c can be configured to be in constant electronic communication with the control system 604, the robotic surgical systems 602a, 602b, 602c can be configured to communicate with the control system 604 at predetermined days/times (e.g., communication occurs every day at 11:00 pm, communication occurs every hour, communication occurs every twelve hours, etc.), or some combination thereof with at least one of the robotic surgical systems 602a, 602b, 602c being configured to communicate constantly and at least one of the robotic surgical systems 602a, 602b, 602c being configured to communicate periodically. As will be appreciated by a person skilled in the art, a robotic surgical system can be configured to communicate constantly without communicating 100% of the time due to any of a variety of factors, such as limitations in processing speed, limitations in network capability, etc.

The networked system 600 in this illustrated embodiment includes three robotic surgical systems 602a, 602b, 602c configured to electronically communicate with the control system 604, but any number of robotic surgical systems (e.g., one, two, ten, twenty, fifty, two hundred, five hundred, etc.) can be configured to electronically communicate with the control system 604. In an exemplary embodiment, a plurality of robotic surgical systems can be configured to electronically communicate with the control system 604, which can help the control system 604 gather data related to a variety of different users, since different robotic surgical systems are typically used by different users. The control system 604 can thus be configured to receive more statistically significant data from the robotic surgical systems, which can facilitate analysis and use of the data, as will be appreciated by a person skilled in the art.

It will be appreciated by a person skilled in the art that the networked system 600 can include security features such that the aspects of the system 600 available to any particular one of the robotic surgical systems 602a, 602b, 602c can be determined based on the identity of the robotic surgical system 602a, 602b, 602c (e.g., an identity of a user using the robotic surgical system, an identification number of the robotic surgical system, etc.) and/or the location from which the system 600 is being accessed (e.g., from a particular IP address, etc.). For example, each user can have a unique username, password, and/or other security credentials to facilitate access to the networked system 600. The received security parameter information can be checked against a database of authorized users to determine whether the user is authorized and to what extent the user is permitted to interact with the system 600, view information stored in the system 600, and so forth. It will be appreciated by a person skilled in the art that the networked system 600 can include security features to enhance overall security, such as by using encryption.

Each of the first, second, and third robotic surgical systems 602a, 602b, 602c can generally be configured and used similar to the robotic surgical systems described above that can include at least one arm. In an exemplary embodiment, each of the first, second, and third robotic surgical systems 602a, 602b, 602c can include at least one movement mechanism (e.g., at least one arm) configured to couple to a surgical instrument, which can be configured to be inserted into a patient through a trocar.

Each of the first, second, and third robotic surgical systems 602a, 602b, 602c can have a variety of configurations. In an exemplary embodiment, each of the robotic surgical systems 602a, 602b, 602c can be robotic surgical systems of the same type (e.g., the same model by the same manufacturer) so as to each have a same configuration, which can help ensure that the data received at and analyzed by the control system 604 is consistently formatted across the robotic surgical systems 602, 602b, 602c and/or includes data for the same parameters for all the robotic surgical systems 602, 602b, 602c.

Figure 11A:
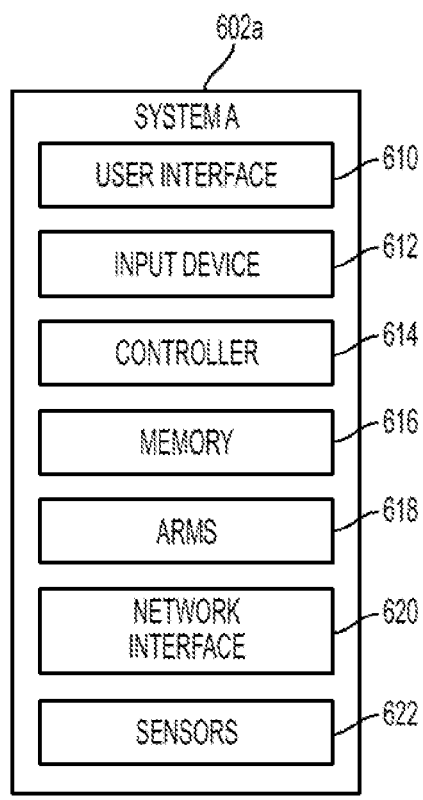
FIG. 11A is a schematic view of one of the plurality of robotic surgical systems of FIG. 11.

FIG. 11A illustrates one embodiment of the first robotic surgical system 602a. As in this illustrated embodiment, the first robotic surgical system 602a can include a user interface 610 (e.g., a GUI on a display, etc.) configured to facilitate interaction of a user with the first robotic surgical system 602a, one or more arms 618, an input device 612 configured to facilitate user control of the arms 618, a controller 614 configured to generally control operation of the robotic surgical system 602a, a memory 616 configured to store data, a network interface 620 configured to facilitate communication over the network 606, and one or more sensors 622. The first robotic surgical system 602a can include additional features, as discussed herein, such as one or more motors, one or more additional input devices, one or more IO interfaces, etc. In general, the controller 614 can be configured to receive an input from a user requesting movement of one or more of the arms 618, relative to a patient, so as to move a surgical instrument (not shown) coupled to the arm(s) 618 for which movement was requested. The user can provide the input using the input device 612, as described herein. The controller 614 can be configured to cause movement of the requested arm(s) 618, thereby causing the movement of the surgical instrument requested by the user.

The one or more sensors 622 can be configured to sense movement of the one or more arms 622, as will be appreciated by a person skilled in the art, such as by sensing position and orientation information in a 3-D coordinate system for the arm, by sensing position and orientation information in a 3-D coordinate system for the surgical instrument coupled to the arm, by sensing position and orientation information in a 3-D coordinate system for a trocar through which the surgical instrument coupled to the arm has been inserted into a patient, etc. The sensor(s) 622 can be configured to communicate the sensed information to the controller 614. The controller 614 can be configured to store the received sensed data in the memory 616 for later communication to the control system 604 (such that the memory 616 serves at least in part as a storage device) and/or to cause the sensed data to be communicated over the network 606 without the sensed data first being stored in the memory 616.

In an exemplary embodiment, the second and third robotic surgical systems 602b, 602c can each be configured similar to the first robotic surgical system 602a, e.g., each configured similar to that shown in FIG. 11A for the first robotic surgical system 602a.

Referring again to FIG. 11, the control system 604 can generally be configured as a computer system. As in this illustrated embodiment, the control system 604 can include a data repository 624 (e.g., a storage device) configured to store data therein, data analytics 626 (e.g., a controller) configured to analyze data, and a data output 628 configured to output 630 results from the data analytics 626 to the data repository 624 for storage therein. The control system 604 can include additional features of a computer system, as discussed herein, such as a network interface, an IO interface, etc.

The data repository 624 can store any one or more types of data therein. The data repository 624 can store data received from the first, second, and third robotic surgical systems 602a, 602b, 602c, e.g., data sensed by sensors thereof; one or more algorithms therein that the data analytics 626 can execute to analyze other data stored in the data repository 624, e.g., the data from the first, second, and third robotic surgical systems 602a, 602b, 602c; one or more baselines (also referred to herein as a "model profiles") each indicative of a recommended initial setup of a robotic surgical system for a surgical procedure; security data (e.g., user identification data, encryption keys, etc.); patient medical data; hospital identification data, site identification data; geographical regions; robotic surgical system type data; day/time; counters; etc.

Different robotic surgical system setups may be preferable for different surgical procedures for a variety of reasons, e.g., because different surgical procedures may require access to different portions of a patient's anatomy, because different surgical procedures may require different angular approaches, because different surgical procedures may use a different number of surgical instruments at a time, etc. In an exemplary embodiment, the data repository 624 can be configured to store therein a plurality of baselines, each of the baselines being indicative of a recommended initial setup of a robotic surgical system for a particular type of surgical procedure. Each of the plurality of baselines can thus be associated with a particular type of surgical procedure, thereby allowing each of the baselines to reflect the particular needs of its associated procedure, e.g., the anatomy access needed therefor, the number of surgical instruments needed therefor, etc., that can affect initial robotic surgical system setup for that procedure. Using different types of gastric surgical procedures as an example, the data repository 624 can be configured to store a baseline for a Roux en-Y gastric bypass procedure, a baseline for a mini gastric bypass (MGB) procedure, a baseline for a duodenal switch procedure, a baseline for a sleeve gastrectomy procedure, a baseline for a gastric band procedure, etc. Using different types of soft tissue repair procedures as another example, the data repository 624 can be configured to store a baseline for a rotator cuff repair procedure, a baseline for an anterior cruciate ligament (ACL) reconstruction procedure, a baseline for an articular cartilage repair procedure, etc.

Although a baseline for a particular type of surgical procedure may be universally useful as an indicator of how to setup a robotic surgical system for that particular procedure, any one or more factors can affect the universal applicability of a baseline for a particular type of surgical procedure. The factors can be patient-based, such as patient size (e.g., weight, height, etc.), anatomical variation, and patient physiology. The factors can be surgical setting-based, such as operating room configuration and operating room space. The factors can be staffing-based, such as number of personnel available to perform a procedure, number of personnel a surgeon prefers to have present, and preferred locations of personnel within the room during procedure performance. The factors can be equipment-based, such as equipment available in a particular operating room, equipment available at a particular hospital, surgeon equipment type preferences, and surgeon equipment brand preferences.

The baselines stored in the data repository 624 can each have one or more characteristics associated therewith. Each of the baselines can have a procedure type characteristic associated therewith that indicates the type(s) of surgical procedure for which the baseline is appropriate, e.g., a first baseline including a procedure type characteristic indicating that it is associated with a sleeve gastrectomy procedure, a second baseline including a procedure type characteristic indicating that it is associated with an ACL reconstruction procedure, a third baseline including a procedure type characteristic indicating that it is associated with a cholecystectomy, etc. Each of the baselines can thus be selected by the data analytics 626 as being appropriate for a particular type of surgical procedure to be performed using one of the robotic surgical systems 602a, 602b, 602c. In addition to the procedure type characteristic, each of the baselines can have one or more additional characteristics associated therewith that each reflect one of the factors that can affect the universal applicability of a baseline for a particular type of surgical procedure. Each of the baselines can thus be coded with a plurality of characteristics that uniquely characterize each of the baselines, which can facilitate analysis of the baselines by the data analytics 626. Examples of the additional characteristics includes characteristics related to patient-based factors (e.g., a patient size characteristic indicating a size of patient appropriate for the baseline, an anatomical variation characteristic indicating a patient anatomy appropriate for the baseline, and a patient physiology characteristic indicating a patient physiology appropriate for the baseline), characteristics related to staffing-based factors (e.g., an operating room characteristic indicating an operating room configuration appropriate for the baseline and a space characteristic indicating an operating room space appropriate for the baseline), characteristics related to staffing-based factors (e.g., a personnel number characteristic indicating a number of personnel appropriate for the baseline and a personnel location characteristic indicating locations of personnel within the room during procedure performance that are appropriate for the baseline), and characteristics related to equipment-based factors (e.g., an equipment type characteristic indicating types of equipment needed for the baseline and an equipment brand characteristic indicating the equipment brand associated with for the baseline).

Each of the baselines can provide a recommendation of an initial setup of a robotic surgical system, e.g., one of the robotic surgical systems 602a, 602b, 602c. In general, the recommended initial setup can help allow the robotic surgical system to be set up appropriately at the outset of a surgical procedure, can reduce surgery setup time since a setup suggestion is provided for the robotic surgical system at least as a place for its setup to start if not end, can make adjustments of the robotic surgical system less likely to be needed after performance of the surgical procedure begins (e.g., adjustment of angular positions of any of the robotic surgical system's arms, changing attachment location of any of the robotic surgical system's arms, etc.), and/or can reduce a number of collisions involving the robotic surgical system's arm(s) due to strategic initial setup as recommended by the baseline.

The recommended initial setup can include various types of information related to initial setup of the robotic surgical system. Each of the baselines can include any one or more types of information. One type of information that can be included in the baseline includes a recommendation of an initial position of each of the one or more arms of the robotic surgical system, such as a recommended initial position of each of the one or more arms relative to one another (inapplicable if the robotic surgical system only includes one arm) and/or relative to a patient on whom a surgical procedure is to be performed using the robotic surgical system being set up. Arms can be multi-jointed, as discussed above. Thus, when a robotic surgical system includes one or more multi-jointed arms, the recommended initial position of each of the one or more multi-jointed arms can include recommended positions of each of the multi-jointed arms' joints, e.g., direction and angle value at which each joint should be bent.

Another type of information that can be included in the baseline includes recommendation of an initial position of each of a plurality of trocars relative to the patient on whom the surgical procedure is to be performed using the robotic surgical system. As discussed herein, each of the robotic surgical system's one or more arms can be configured to couple to a surgical instrument, which can each be configured to be inserted into a patient through a trocar. Thus, providing recommended initial setup positions of trocars to be used in the surgical procedure, e.g., where the trocars should be advanced through skin of the patient and/or an angular orientation of the surgical instruments, can inform the initial setup of the robotic surgical system in order for the one or more surgical instruments coupled to the robotic surgical system's one or more arms to be insertable through the trocars and into the patient.

Baselines associated with surgical procedures using one trocar, e.g., as coded in the baselines' characteristics, can include a recommended initial position for the one trocar. Baselines associated with surgical procedures using multiple trocars, e.g., as coded in the baselines' characteristics, can include a recommended initial position for each of the trocars. Some surgical procedures may be performed using one trocar, while other surgical procedures may be performed using multiple trocars. For example, in a MIS procedure, a single trocar may be used to advance a surgical instrument therethrough including a camera and having at least one working channel extending therethrough through which another surgical instrument can be inserted. For another example, in a MIS procedure, a first trocar may be used to advance a tissue manipulating tool (e.g., a grasper, a retractor, a knife, a stapler, a cautery tool, etc.) into the patient, and a second trocar may be used to insert a camera into the patient to allow visualization of the tissue manipulating tool. Proper location of the trocars relative to the patient can help ensure that the camera maintains visualization of the tissue manipulating tool as appropriate during the MIS procedure. For yet another example, in a MIS procedure, a first trocar may be used to advance a first tissue manipulating tool into the patient, and a second trocar may be used to advance a second tissue manipulating tool into the patient, with the first and second tools being used in cooperation to manipulate tissue. Proper location of the trocars relative to the patient can help ensure that the first and second tools can access the tissue without obstructing each other and without damaging any other matter inside the patient's body. A third trocar may be used to advance a camera into the patient, with the location of the third trocar helping to ensure that the camera can visualize both of the first and second tools as appropriate during their use.

Another type of information that can be included in the baseline includes a recommendation of an attachment location of each of the one or more arms of the robotic surgical system to a stationary item. The attachment locations of the one or more arms can thus be less likely to need to be moved to another location during performance of the surgical procedure, which can be time-consuming and/or difficult due to movement of the patient and/or other items thus far in the surgical procedure.

Another type of information that can be included in the baseline includes a recommendation of an initial position of each of the one or more surgical instruments configured to be coupled to the robotic surgical system, such as a recommended initial position of each of the surgical instruments relative to one another (inapplicable if the robotic surgical system only includes one arm) and/or relative to a patient on whom a surgical procedure is to be performed using the robotic surgical system being set up. As discussed herein, each of the robotic surgical system's one or more arms can be configured to couple to a surgical instrument. Thus, providing recommended initial setup positions of the surgical instrument(s) to be coupled to the arm(s) and used in the surgical procedure, e.g., where the surgical instruments should be advanced through skin of the patient and/or an angular orientation of the surgical instruments, can inform the initial setup of the robotic surgical system in order for the one or more surgical instruments coupled to the robotic surgical system's one or more arms to be insertable into the patient.

A baseline can be provided by the control system 604 to a robotic surgical system for which the recommended initial setup is intended in any one or more of a variety of ways. In an exemplary embodiment, the recommended initial setup can be provided on a display electronically coupled to the robotic surgical system for which the recommended initial setup is intended. The display can be an integral part of the robotic surgical system, e.g., a screen built thereon, etc., or the display can include a discrete display electronically coupled to the robotic surgical system by a wired or wireless connection via an IO interface of the robotic surgical system, e.g., a display of a mobile phone, a display of a laptop computer, etc. The recommended initial setup can be provided on the display as text, as one or more still images, and/or as one or more moving images (e.g., video). In at least some embodiments, audio regarding the recommended initial setup can be provided to supplement the display, e.g., audio played through a speaker electronically coupled to the robotic surgical system.

Figure 12:
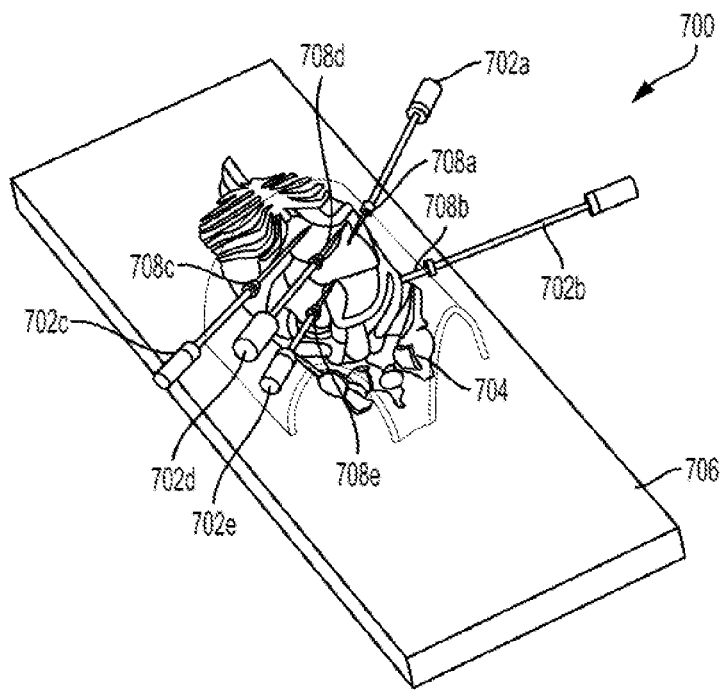
FIG. 12 is a perspective view of one embodiment of a display of a recommended initial setup of a plurality of trocars and a plurality of surgical instruments with respect to a patient.

FIG. 12 illustrates one embodiment of a visual display of a recommended initial setup 700 for a robotic surgical system to be used in performed of a surgical procedure on a patient, which in this illustrated embodiment includes an abdominal MIS procedure. In this illustrated embodiment, the recommended initial setup 700 includes recommended initial positions of a plurality of surgical instruments 702a, 702b, 702c, 702d, 702e relative to one another, relative to a partial representation 704 of the patient so as to show the instruments' recommended position relative to the patient, and relative to a representation 706 of a table on which the patient rests during the procedure, and the recommended initial setup 700 includes recommended initial positions of a plurality of trocars 708a, 708b, 708c, 708d, 708e (through which the instruments 702a, 702b, 702c, 702d, 702e are respectively inserted into the patient) relative to one another, relative to the representation 704 of the patient, and relative to the representation 706 of the table. The recommended initial setup 700 can be configured to be manipulated by a user (e.g., using the user interface 610) in any number of ways, such as by allowing the user to rotate the image of the recommended initial setup 700, by allowing the user to selectively apply filters enabling only one of the recommended instrument positions and the recommended trocar positions to be shown at a time or for both the recommended instrument positions and the recommended trocar positions to be shown at a time (as in FIG. 12), and/or by allowing the user to play the supplemental audio on demand.

Figure 13:
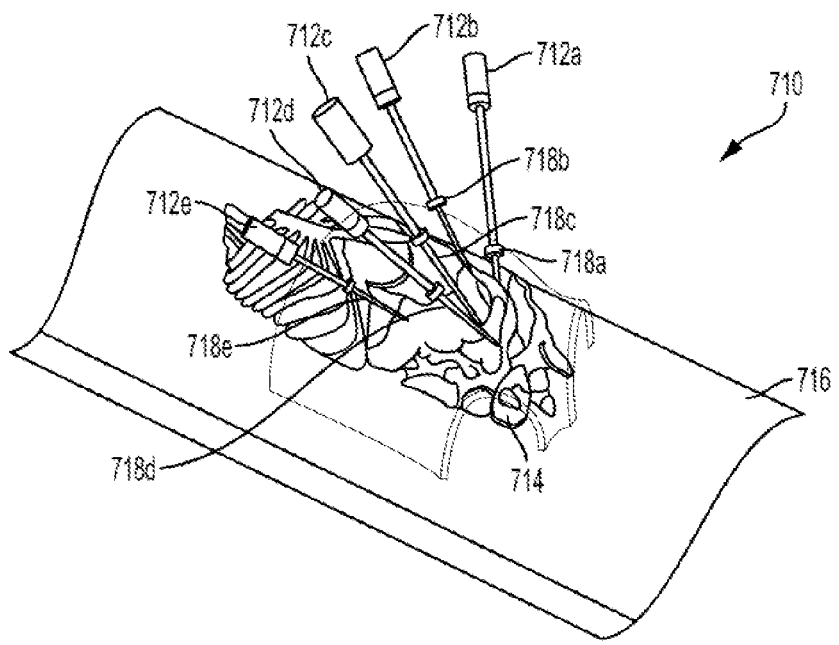
FIG. 13 is a perspective view of another embodiment of a display of a recommended initial setup of a plurality of trocars and a plurality of surgical instruments with respect to a patient.

FIG. 13 illustrates another embodiment of a visual display of a recommended initial setup 710 for a robotic surgical system to be used in performed of a surgical procedure on a patient, which in this illustrated embodiment includes an abdominal MIS procedure (a different type of procedure than in the embodiment of FIG. 12). In this illustrated embodiment, the recommended initial setup 710 includes recommended initial positions of a plurality of surgical instruments 712a, 712b, 712c, 712d, 712e relative to one another, relative to a partial representation 714 of the patient so as to show the instruments' recommended position relative to the patient, and relative to a representation 716 of a table on which the patient rests during the procedure, and the recommended initial setup 710 includes recommended initial positions of a plurality of trocars 718a, 718b, 718c, 718d, 718e (through which the instruments 712a, 712b, 712c, 712d, 712e are respectively inserted into the patient) relative to one another, relative to the representation 704 of the patient, and relative to the representation 706 of the table. The recommended initial setup 710 can be configured to be manipulated by a user, similar to that discussed above regarding the recommended initial setup 700 of FIG. 12.

Referring again to FIG. 11, the control system 604 can be configured to provide one or more recommended initial setups for a surgical procedure to be performed using a robotic surgical system, e.g., using one of the first, second, and third robotic surgical systems 602a, 602b, 602c. Providing only one recommended initial setup can help reduce user indecision and uncertainty in how to initially set up the robotic surgical system. Providing a plurality of recommended initial setups can allow the user to choose which one of the recommended initial setups best meets the user's preferences (e.g., is most appropriate for the particular surgical procedure, is most appropriate for the particular patient, best aligns with surgeon preferences, etc.) and/or can help the control system 604 accommodate situations in which the control system's data repository 624 does not have stored therein a baseline that precisely corresponds to the surgical procedure to be performed and/or to characteristics of the procedure as input to the control system 604 but the data repository 624 has two or more baselines that are close. In at least some embodiments, the control system 604 can be configured to identify one of the plurality of provided recommended initial setups as a default, or preferred, setup to the user. The default can be a one of the recommended initial setups that has characteristics most closely corresponding to characteristics of the surgical procedure to be performed using the robotic surgical system.

The control system 604 can be configured to receive data indicative of the characteristics of the surgical procedure to be performed by the robotic surgical system. In an exemplary embodiment, the data can be input by a user to the robotic surgical system, e.g., via the user interface 610, and transmitted to the control system 604 over a communication line, e.g., the one of the communications lines 608a, 608b, 608c associated with the one of the robotic surgical systems 602a, 602b, 602c intended to perform the procedure. The data analytics 626 can be configured to determine which one or more of the baselines stored in the data repository 624 to provide as the recommended initial setups based at least in part on the received data indicative of the procedure's characteristics, e.g., based on a type of the procedure to be performed, on a number of personnel available to perform the procedure, etc. The data analytics 626 can be configured to match the input characteristics with those of the stored baselines' characteristics and determine which of the baselines have characteristics that precisely match the input characteristics and choose those one or more baselines to provide to the user as recommendations. If no baselines have characteristics that precisely match the input characteristics, the data analytics 626 can be configured to choose one or more best baseline matches, e.g., the one or more baselines that have characteristics matching the most of the input characteristics.

The control system 604 can be configured to facilitate setup of the robotic surgical system to be used in performance of the surgical procedure for which the one or more recommended initial setups have been provided. In other words, the control system 604 can be configured to help the user achieve the recommended initial setup, e.g., help the user initially place trocars in accordance with the baseline, help the user initially place robotic surgical system arms in accordance with the baseline, help the user attach robotic surgical system arms to stationary item(s) at certain location(s) in accordance with the baseline, help the user position surgical instruments in accordance with the baseline, etc. In general, once one or more recommended initial setups have been provided to a user, and, in the case of a plurality of recommended initial setups being provided as options that the user can choose among, once a recommended initial setup has been chosen by the user, the control system 604 can be configured to aid the user in setting up the surgical procedure in accordance with the one provided baseline or with the selected one of a plurality of provided baselines.

The robotic surgical system can be configured to facilitate its setup in accordance with the recommended initial setup in a variety of ways. Any one or more of the ways can be provided in conjunction with a provided baseline. For example, an actual position of trocar(s) can be provided with the recommended positions of the trocar(s) contained in the baseline. The user can thus more easily match the position of the actual trocar(s) to their recommended positions, more easily interpret the recommended trocar positions, and/or more easily mimic the setup of the robotic surgical system's arms in accordance with the recommended trocar positions. The control system 604 can be configured to cause the actual position of trocar(s) to be provided in a variety of ways. In an exemplary embodiment, the actual position of the trocar(s) can be provided on a display electronically coupled to the robotic surgical system for which the recommended initial setup is intended, such as by showing a camera image of the actual trocar(s). In at least some embodiments, the actual position of the trocar(s) and the recommended position of the trocar(s) can be provided as superimposed images on the display, which can help facilitate matching of actual trocar positions to recommended trocar positions and help the robotic surgical system's arms be positioned to accommodate the recommended trocar positions (e.g., so a surgical instrument coupled to an arm can be inserted through the trocar in the recommended position). One of the superimposed images, e.g., one of the actual trocar images and the recommended trocar images, can be ghosted on the display to help the user identify which image the user can affect and which image the user is mimicking.

For another example, an actual position of surgical instruments can be shown with the recommended positions of the surgical instruments contained in the baseline. The user can thus more easily match the position of the actual instrument(s) to their recommended positions, more easily interpret the recommended instrument positions, and/or more easily mimic the setup of the robotic surgical system's arms in accordance with the recommended instrument positions. The control system 604 can be configured to cause the actual position of instrument(s) to be provided in a variety of ways, such as those similar to those discussed above for causing the actual position of trocar(s) to be provided to the user.

For yet another example, each of the arms of the robotic surgical system to be used in performing the surgical procedure can include at least one position, location, or orientation indicator (e.g., a graphic printed thereon, coordinate axes printed thereon, etc.) that can help the user match the initial position of each arm to the recommended initial position thereof. At least one feedback mechanism, e.g., a light, a sound, a vibration, etc., can be provided in addition to the one or more indicators to further facilitate achievement of the recommended initial setup. The feedback mechanism(s) can be configured to instruct the user which of the robotic surgical system's arms still needs adjustment to achieve their recommended positions, e.g., a light on an arm remains illuminated until the arm's position matches the baseline, etc. The robotic surgical system can include the at least one feedback mechanism, e.g., one or more lights thereon, etc.

For another example, the robotic surgical system can be configured to automatically position its arms in accordance with the recommended initial setup. The robotic surgical system, e.g., the controller thereof, can be configured to receive baseline data from the control system 604 indicative of the baseline's recommended position, location, and orientation of each of the robotic surgical system's arms. The robotic surgical system, e.g., the controller thereof, can be configured to interpret the baseline data to cause each of the robotic surgical system's arms to move to that arm's recommended position, location, and orientation, e.g., by driving one or more motors of the robotic surgical system to move each of the arms as needed to achieve the recommended initial setup. The robotic surgical system being configured to automatically position its arms in accordance with the recommended initial setup can help the arms be positioned precisely as recommended and/or can help save the user's time since the user need not manually move the arms.

For still another example, the robotic surgical system can be configured to guide the user in manually positioning each of the robotic surgical system's arms in accordance with the recommended initial setup. Each of the arms can be configured to resist motion in a direction away from the arm's recommended setup (e.g., using force feedback or tactile feedback), configured to aid motion in a direction toward the arm's recommended setup (e.g., using force feedback or tactile feedback), and configured to lock in position when it reaches its recommended setup. Each of the arms can include a mechanical and/or electrical locking mechanism configured to cause the lock in position. The robotic surgical system can be configured to allow user override of the locking mechanism, e.g., for safety reasons.

The baselines stored in the data repository 624 can be preprogrammed therein, can be dynamically created by the control system 604 from any one or more data sources, and/or a combination thereof. By being preprogrammed, a first use of the control system 604 can allow a baseline to be provided thereby to a robotic surgical system. The preprogrammed baselines can be based on other baselines in other control systems and/or can be created based on expert knowledge and/or experience, e.g., experiences of surgeons in performed surgical procedures, etc.

Dynamic creation of baselines can allow the baselines to reflect actual performances of surgical procedures and/or can facilitate the baselines reflecting experiences of numerous users. The control system 604 can be configured to gather data from the plurality of robotic surgical systems 602a, 602b, 602c in communication therewith regarding the performance of surgical procedures using the robotic surgical systems 602a, 602b, 602c and to analyze the data to create the baselines using the data. The control system 604 must therefore gather data before any baselines can be provided thereby. Alternatively to creating the baselines from scratch, baselines can be preprogrammed into the control system 604 (e.g., into the data repository 624), and the control system 604 can be configured to dynamically adjust the baselines therein based on the data gathered from the plurality of robotic surgical systems 602a, 602b, 602c in communication therewith regarding the performance of surgical procedures using the robotic surgical systems 602a, 602b, 602c. The control system 604 can thus be configured to provide a baseline upon a first use of the control system 604, e.g., because baselines are preprogrammed therein, and can be configured to modify the baselines in accordance with actually performed surgical procedures, thereby allowing the baselines to improve in accuracy over time as they are adjusted based on actual experiences.

The control system 604 (e.g., the data analytics 626) can be configured to analyze data received from the plurality of robotic surgical systems 602a, 602b, 602c in communication therewith regarding the performance of surgical procedures using the robotic surgical systems 602a, 602b, 602c in a variety of ways. In general, as will be appreciated by a person skilled in the art, the control system 604 can be configured to analyze the data using any one or more statistical and/or mathematical calculations, such as root mean square calculations, mean absolute deviation calculations, regression analysis, crest factor and form factor calculations, spatial analysis, etc. The use of statistical and/or mathematical calculations for particular application can be chosen depending on the particular application, as will be appreciated by a person skilled in the art.

Figure 14:
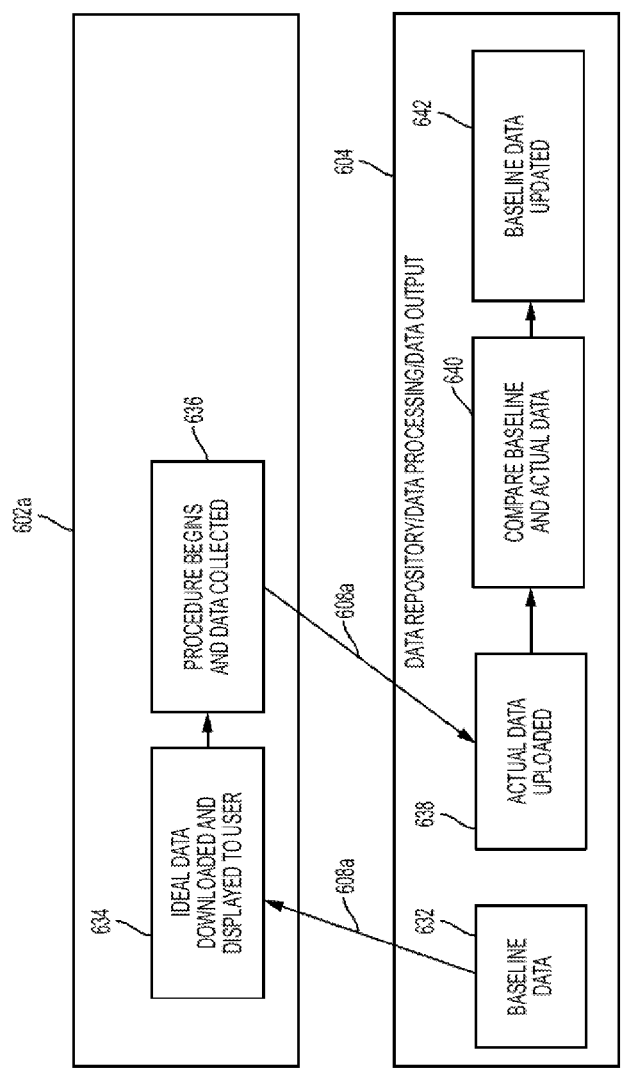
FIG. 14 is a schematic view of one embodiment of a method of using a networked system such as the networked system of FIG. 11.

FIG. 14 illustrates an embodiment of a method of using the control system 604 that includes modifying a stored baseline based on data gathered from the first robotic surgical system 602a in communication therewith. The first robotic surgical system 602a is merely an illustrative example in FIG. 14. The method can be similarly performed with respect to any robotic surgical system in electronic communication with the control system 604. Additionally, the method can be similarly performed with other embodiments of control systems described herein.

As in this illustrated embodiment, the control system 604 can transmit 632 baseline data indicative of a baseline stored in the data repository 624 to the first robotic surgical system 602a over the first communication line 608a. The baseline data can be transmitted to the first robotic surgical system 602a in response to a request transmitted therefrom to the control system 604. The first robotic surgical system 602a can receive 634 the transmitted baseline data (also referred to herein as "ideal data" as being indicative of an ideal setup of the robotic surgical system) and provide 634 the baseline to a user of the first robotic surgical system 602a. As mentioned above, in an exemplary embodiment, providing the baseline to the user can include displaying the baseline on a display of the first robotic surgical system 602a. The first robotic surgical system 602a can be setup in accordance with the baseline (which, as discussed above, can be either the only baseline provided or a selected one of a plurality of provided baselines), as discussed herein. The user has the option of deviating the first robotic surgical system's initial setup from the initial setup recommended in the baseline, which can facilitate accommodation of surgeon preferences and/or can facilitate accommodation of characteristic(s) of the surgical procedure to be performed that the user believes may not be fully reflected in the baseline (e.g., a number of personnel for the surgical procedure has changed since the baseline was provided by the control system 604, the equipment to be used in the surgical procedure has unexpectedly changed, etc.).

With the first robotic surgical system 602a setup to the user's satisfaction, the surgical procedure can be performed 636 using the first robotic surgical system 602a, and data regarding the procedure's performance can be collected 636 by the first robotic surgical system 602a. The collected data can be stored in the first robotic surgical system's memory 616 before being transmitted 638 to the control system 604, or the collected data can be transmitted 638 to the control system 604 without first being stored locally in the first robotic surgical system's memory 616. Storing the collected data in the memory 616 prior to transmission 636 can help the data be transmitted more efficiently, as will be appreciated by a person skilled in the art. The collected data can include a variety of different data parameters that can, in general, facilitate creation and/or modification of the stored baselines. Examples of the collected data include patient-specific data (e.g., scanned images, biometrics, etc.), arm movement data (e.g., coordinate data for each of the arms at various times throughout the performance of the procedure, arm movement speed, etc.), arm collision data (e.g., time stamp of when any of the robotic surgical system's arms collides with another object), instrument collision data (e.g., time stamp of when any of the instruments coupled to robotic surgical system's arms collides with another object), and surgical instrument movement data (e.g., time stamp of when any of the robotic surgical system's instruments collides with another object, instrument movement speed, etc.). In an exemplary embodiment, all or some the data can be collected automatically by the first robotic surgical system 602a, e.g., using the sensors 622, using the input device 612, using an image scanner (e.g., CT images, x-ray images, etc.), etc., and all of some of the data can be collected via user input (e.g., input via the user interface 610, scanning of a barcode on a surgical instrument, scanning of a radio frequency identification (RFID) chip in a surgical instrument, etc.). Collisions can be detected in a variety of ways, as will be appreciated by a person skilled in the art, such as by detecting when an amount of current supplied to an arm exceeds a predetermined threshold amount of current, thereby indicating that the arm is attempting to be driven by a motor but is having difficulty moving much if at all because the arm is being obstructed by another object.

The first robotic surgical system 602a and/or the control system 604 can be configured to tag (e.g., electronically mark or flag) collected data that may be indicative of an alarm condition. The tags can help the control system 604 and/or the user analyze the surgical procedure to, e.g., evaluate efficiencies thereof, determine why a problem occurred during the procedure, adjust the baseline used for the surgical procedure, etc. Examples of alarm conditions in the collected data that the first robotic surgical system 602a and/or the control system 604 can be configured to tag include a joint of a multi-jointed arms reaching a joint limit, movement speed exceeding a predetermined threshold maximum speed, spatial coordinate being outside a predetermined threshold coordinate space, an arm collision, an instrument collision, etc. The control system 604 can thus be configured to receive a record of types of alarm conditions that occurred during the performance of the surgical procedure, a total number of alarm conditions that occurred during the performance of the surgical procedure, a number of each type of alarm condition that occurred during the performance of the surgical procedure, and when each alarm condition occurred during the performance of the surgical procedure.

The control system 604 can be configured to compare 640 the baseline used for the surgical procedure with at least some of the data received 638 from the first robotic surgical system 602a. As will be appreciated by a person skilled in the art, and as mentioned above, the control system 604 can be configured to compare the data using any one or more statistical and/or mathematical calculations. Based on the comparison, the control system 604 can be configured to modify 642 the baseline used for the surgical procedure, thereby allowing the baseline to reflect actual user experience and at least potentially improve the next use of the baseline in a surgical procedure performed using any of the robotic surgical systems 602a, 602b, 602c in communication with the control system 604. Based on the alarm conditions tagged in the data received 638 by the control system 604, the control system 604 can adjust 642 the baseline used for the surgical procedure to help prevent any of the tagged alarm conditions from occurring in a subsequently performed surgical procedure that uses the baseline since the baseline as provided for that subsequent procedure will have been modified in view of the previously performed procedure. As discussed herein, the modification 626 can include adjusting any of the types of information included in the baseline, e.g., a recommended initial position of each of a plurality of trocars, a recommendation of an initial position of each of the robotic surgical system's arms, an attachment location of each of the robotic surgical system's arms to a stationary item, an initial position of each of one or more surgical instruments configured to be coupled to the robotic surgical system, etc. At least some comparisons 640 may not result in any modification 642 of the baseline because, e.g., the performed surgical procedure did not include any tagged data indicative of an alarm condition so as to indicate that the recommended initial setup ideally setup the first robotic surgical system 602a.

Figure 15:
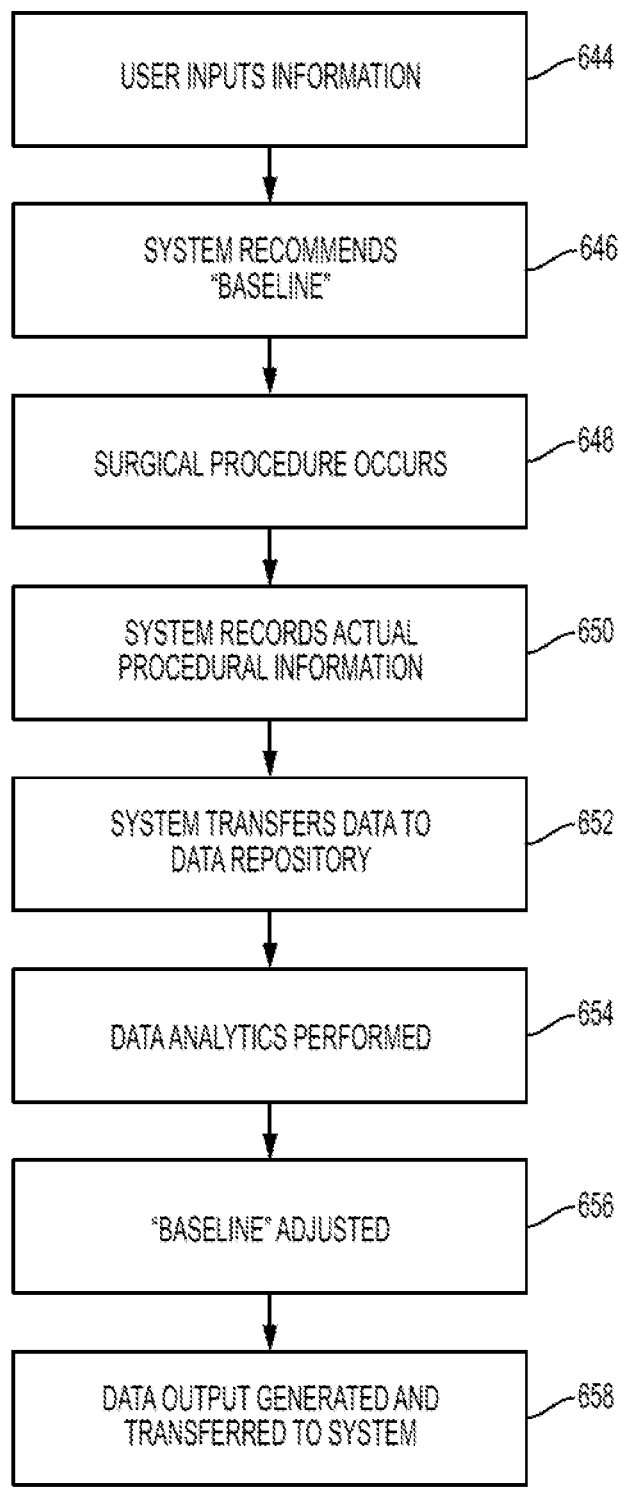
FIG. 15 is a schematic view of another embodiment of a method of using a networked system such as the networked system of FIG. 11.

FIG. 15 illustrates another embodiment of a method of using the control system 604 that includes modifying a stored baseline based on data gathered from one of the robotic surgical system 602a, 602b, 602c in communication therewith. For ease of discussion, the first robotic surgical system 602a is discussed below with respect to the method of FIG. 15, but the method can be similarly performed with respect to any robotic surgical system in electronic communication with the control system 604. Additionally, the method can be similarly performed with other embodiments of control systems described herein.

As in this illustrated embodiment, a user of the first robotic surgical system 602a can input 644 information regarding the surgical procedure to be performed so as to include preliminary data, e.g., data input prior to performance of the surgical procedure. As discussed herein, the data can be input 644 in a variety of ways (e.g., via the user interface 610, etc.) and can include any one or more types of data (e.g., patient-specific data, instrument data, personnel data, etc.). In an exemplary embodiment, the input 644 data includes at least one characteristic of the surgical procedure to be performed. The at least one input characteristic can facilitate the control system's selection of one or more baselines stored therein to provide 646 to the first robotic surgical system 602a by allowing the input characteristic(s) to be compared to the stored baselines' characteristics. The first robotic surgical system 602a can be setup in accordance with the baseline (which, as discussed above, can be either the only baseline provided or a selected one of a plurality of provided baselines), as discussed herein, with the user having the option of deviating the first robotic surgical system's initial setup from the initial setup recommended in the baseline.

With the first robotic surgical system 602a setup to the user's satisfaction, the surgical procedure can be performed 648 using the first robotic surgical system 602a, and data regarding the procedure's performance can be collected 650 by the first robotic surgical system 602a. The collected data can be transmitted 652 from the first robotic surgical system 602a to the control system 604, which can store the received data in the data repository 624. The control system 604, e.g., the data analytics 626, can analyze 654 the received data and modify 656 the baseline used for the surgical procedure in accordance with the analysis. In general, the control system 604 can be configured to modify 656 the baseline in response to any alarm conditions that occurred during performance of the surgical procedure, since alarm conditions generally reflect an undesired event occurring during performance of the surgical procedure. The modified baseline can be output (e.g., via the data output 628) and stored 658 in the data repository 624, from which it can be provided to the first robotic surgical system 602a or any other of the robotic surgical systems 602b, 602c in communication with the control system 604 for use in another surgical procedure.

Figure 16:
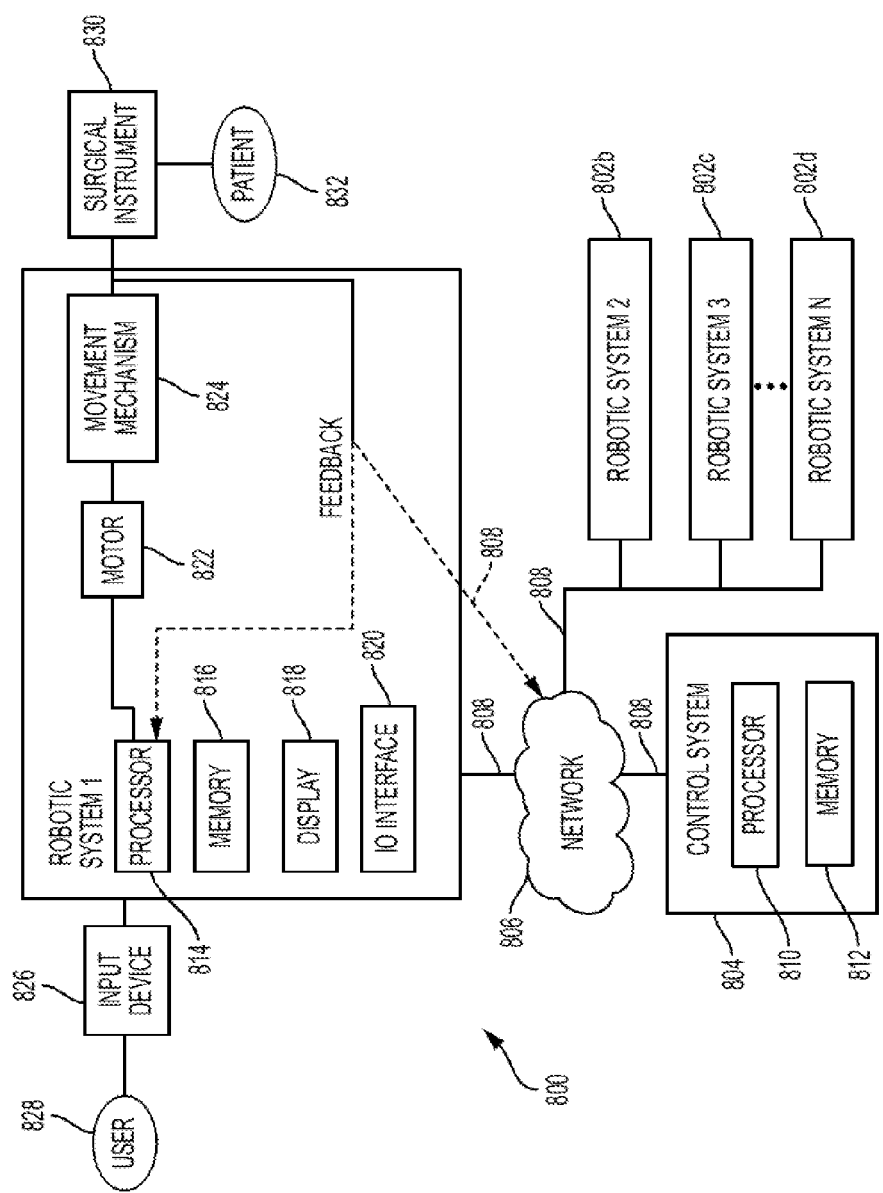
FIG. 16 is a schematic view of another embodiment of a networked system including a control system and a plurality of robotic surgical systems.

FIG. 16 illustrates another embodiment of a networked system 800 configured to facilitate the collection of data from a plurality of robotic surgical systems 802a, 802b, 802c, 802d (where "N" in FIG. 16 is N≥4) and to facilitate determination of a recommended robotic surgical system setup based at least in part on the collected data. The networked system 800 can generally be configured and used similar to the networked system 600 of FIG. 11. In this illustrated embodiment, the network system 800 includes a control system 804 configured to communicate with the plurality of robotic surgical systems 802a, 802b, 802c, 802d over a network 806 using one or more communication lines 808. In this illustrated embodiment, the control system 804 can include a processor 810 and a memory 812. In this illustrated embodiment, the first robotic surgical system 802a includes a processor 814, a memory 816, a display 818, an IO interface 820, a motor 822, and a movement mechanism 824. The first robotic surgical system 802a can be configured to electronically communicate with an input device 826 configured to receive input from a user 828. The movement mechanism 824 can be configured to couple to a surgical instrument 830 configured to be inserted into a patient 832. As discussed herein, data can be collected from the first robotic surgical system 802a and fed back thereto and/or to the control system 804. The other robotic surgical systems 802b, 802c, 802d that can communicate with the control system 804 can be configured similar the first robotic surgical system 802a.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for facilitating performance of surgical procedures, comprising:
   a memory configured to store a model profile indicating a suggested setup of a model robotic surgical system for a model surgical procedure, wherein the suggested setup includes a recommendation of an attachment location of each of a plurality of moveable arms of a robotic surgical system to a stationary item, the robotic surgical system to be used in performance of a surgical procedure after the storing of the model profile, wherein the suggested setup includes a recommendation of an initial position of each of the arms of the robotic surgical system, and wherein the arms are each configured to couple to one of a plurality of surgical instruments; and
   a processor configured to, after the plurality of movable arms have been attached to the stationary item in accordance with the recommendation of the attachment location, drive one or more motors of the robotic surgical system to be used in performance of the surgical procedure on a patient and thereby move one or more of the plurality of movable arms such that the one or more of the plurality of movable arms are automatically positioned in accordance with the recommendation of the initial position of each of the arms;
   wherein the processor is also configured to:
      receive movement data indicative of movement of the arms during performance of the surgical procedure on the patient,
      after performance of the surgical procedure, modify the model profile based on the received movement data, and
      store the modified model profile in the memory.

2. The system of claim 1, wherein the modification of the model profile is based at least in part on movement of the arms during performance of the surgical procedure from suggested setup positions of the arms provided in the model profile.

3. The system of claim 1, wherein the modification of the model profile is based at least in part on a number of collisions between any of the arms and another object during performance of the surgical procedure.

4. The system of claim 1, wherein the suggested setup further includes at least one of a recommendation of an initial position of each of a plurality of trocars relative to the patient on whom the surgical procedure is to be performed using the robotic surgical system, and a recommendation of an initial position of each of the plurality of surgical instruments.

5. The system of claim 4, wherein the suggested setup includes at least the recommended initial position of each of the trocars, and each of the surgical instruments coupled to the arms of the robotic surgical system is configured to be inserted into the patient through one of the trocars.

6. The system of claim 4, wherein the suggested setup includes at least the recommended initial position of each of the plurality of surgical instruments, and the recommended initial position of each of the plurality of surgical instruments includes at least one of the instruments' position relative to the patient on whom the surgical procedure is to be performed using the robotic surgical system, and the instruments' position relative to each other.

7. The system of claim 1, wherein the recommended initial position of each of the arms of the robotic surgical system includes at least one of the arms' position relative to the patient on whom the surgical procedure is to be performed using the robotic surgical system, and the arms' position relative to each other.

8. The system of claim 1, wherein the stationary item is selected from the group consisting of a table, a wall, a cart, and a ceiling.

9. The system of claim 1, wherein the memory is configured to store a plurality of model profiles each indicating a suggested setup of the model robotic surgical system and each being associated with a different characteristic;
   the processor is configured to receive preliminary data indicative of a characteristic associated with the surgical procedure to be performed using the robotic surgical system; and
   the processor is configured to, prior to driving the one or more motors, select the model profile from among the plurality of model profiles as the one of the plurality of model profiles associated with the same characteristic as the surgical procedure to be performed on the patient.

10. The system of claim 9, wherein the characteristic associated with the surgical procedure includes a type of the surgical procedure to be performed using the robotic surgical system, a patient anatomy being targeted in the surgical procedure to be performed using the robotic surgical system, a position of a plurality of trocars being used in the surgical procedure to be performed using the robotic surgical system relative to the patient, a position of a person performing at least a portion of the surgical procedure to be performed using the robotic surgical system, a size of the patient, and an anatomical variation of the patient.

11. The system of claim 1, wherein the processor is configured to cause the model profile to be communicated to a user by causing the model profile to be displayed on a display.

12. The system of claim 1, wherein the suggested setup further includes a recommendation of an initial position of at least one joint of each of the arms of the robotic surgical system.

13. The system of claim 1, wherein attaching the plurality of movable arms to the stationary item in accordance with the suggested setup includes user attachment of the arms to the stationary item.

14. A system for facilitating performance of surgical procedures, comprising:
   a processor configured to
      receive, from each of a plurality of robotic surgical systems, position data indicative of an initial position of each of a plurality of electromechanical arms of the robotic surgical system for use during performance of a surgical procedure using the robotic surgical system, each of the plurality of arms being configured to be coupled to a surgical instrument,
      receive, from each of the plurality of robotic surgical systems, collision data indicative of one or more collisions that occur between two or more of the plurality of arms during performance of the surgical procedure using the robotic surgical system, analyze the received position data and the received collision data to determine a recommended initial setup of an intended robotic surgical system for use during performance of a second surgical procedure, the intended robotic surgical system including a plurality of movable arms each configured to couple to one of a plurality of surgical instruments, the recommended initial setup including a recommendation of an initial angular orientation of each surgical instrument relative to each other during the performance of ne surgical procedure, and drive one or more motors of the intended robotic surgical system and thereby move one or more of the plurality of movable arms of the intended robotic surgical system such that the plurality of surgical instruments coupled thereto are automatically positioned in accordance with the recommended initial setup; and a memory configured to store the received position data, the received collision data, and the recommended initial setup.

15. The system of claim 14, wherein the recommended initial setup of the intended robotic surgical system further includes at least one of a recommendation of an initial position of each of a plurality of electromechanical arms of the intended robotic surgical system, a recommendation of an attachment location of each of the electromechanical arms of the intended robotic surgical system to a stationary item, and a recommendation of an initial position of each of a plurality of trocars relative to the patient on whom the surgical procedure is to be performed using the intended robotic surgical system.

16. The system of claim 14, wherein the processor is configured to receive preliminary data indicative of an aspect of the surgical procedure to be performed using the intended robotic surgical system, the analyzing to determine the recommended initial setup including analysis of the preliminary data, the gathered position data, and the gathered collision data.

17. The system of claim 16, wherein the aspect of the surgical procedure includes a type of the surgical procedure to be performed using the intended robotic surgical system, a patient anatomy being targeted in the surgical procedure to be performed using the intended robotic surgical system, a position of a plurality of trocars being used in the surgical procedure to be performed using the intended robotic surgical system relative to the patient, a position of a person performing at least a portion of the surgical procedure to be performed using the intended robotic surgical system, a size of the patient, and an anatomical variation of the patient.

18. The system of claim 14, wherein the processor is configured to receive position data indicative of an initial position of each of the arms of the intended robotic surgical system at a start of the second surgical procedure to be performed using the intended robotic surgical system, receive collision data indicative of one or more collisions that occur between two or more of the plurality of arms of the intended robotic surgical system during the performance of the second surgical procedure using the intended robotic surgical system, analyze the received position data for the plurality of robotic surgical systems, the received position data for the intended robotic surgical system, the received collision data for the plurality of robotic surgical systems, and the received collision data for the intended robotic surgical system, modify the recommended initial setup based on the analysis, and cause the modified recommended initial setup to be provided to a user of a second robotic surgical system for use during performance of a third surgical procedure.

19. The system of claim 14, wherein the processor is configured to cause the recommended initial setup to be provided to a user by causing the recommended initial setup to be displayed on a display.

20. The system of claim 14, wherein the intended robotic surgical system includes the processor.

21. The system of claim 14, wherein a computer system remotely located from the intended robotic surgical system includes the processor.

22. A method for facilitating performance of surgical procedures, comprising:

for each of a plurality of robotic surgical systems, gathering position data indicative of an initial position of each of a plurality of electromechanical arms of the robotic surgical system for use during performance of a surgical procedure using the robotic surgical system, each of the plurality of arms being configured to be coupled to a surgical instrument;

for each of the plurality of robotic surgical systems, gathering collision data indicative of one or more collisions that occur between two or more of the plurality of arms during performance of the surgical procedure using the robotic surgical system;

analyzing the gathered position data and the gathered collision data to determine a recommended initial setup of an intended robotic surgical system for use during performance of a subsequent surgical procedure, the intended robotic surgical system including a plurality of movable arms each configured to couple to one of a plurality of surgical instruments, the recommended initial setup including a recommendation of an initial position of each surgical instrument relative to each other; and driving one or more motors of the intended robotic surgical system and thereby moving one or more of a plurality of movable arms of the intended robotic surgical system such that the plurality of surgical instruments are automatically position in accordance with the recommended initial setup.

* * * * *